(12) United States Patent
Kitahara et al.

(10) Patent No.: US 7,629,471 B2
(45) Date of Patent: Dec. 8, 2009

(54) TRANSCRIPTIONAL FACTOR, PROCESS FOR PRODUCING THE SAME AND USE THEREOF

(75) Inventors: Takeshi Kitahara, Tokyo (JP); Hidenori Watanabe, Nagareyama (JP); Kunio Ando, Kawasaki (JP)

(73) Assignee: NRL Pharma, Inc. (JP)

( * ) Notice: Subject to any disclaimer, the term of this patent is extended or adjusted under 35 U.S.C. 154(b) by 507 days.

(21) Appl. No.: 10/546,854

(22) PCT Filed: Feb. 24, 2004

(86) PCT No.: PCT/JP2004/002110

§ 371 (c)(1), (2), (4) Date: Aug. 24, 2005

(87) PCT Pub. No.: WO2004/074236

PCT Pub. Date: Sep. 2, 2004

(65) Prior Publication Data
US 2006/0247307 A1 Nov. 2, 2006

(30) Foreign Application Priority Data
Feb. 24, 2003 (JP) ............................. 2003-092682

(51) Int. Cl.
*C07D 213/80* (2006.01)
*C07D 211/78* (2006.01)
*A61K 31/34* (2006.01)

(52) U.S. Cl. .................. 546/322; 546/326; 514/356; 514/354

(58) Field of Classification Search .......... 546/322, 546/326; 514/356, 354, 471
See application file for complete search history.

(56) References Cited

U.S. PATENT DOCUMENTS
6,413,507 B1 * 7/2002 Bentley et al. ........... 424/78.02

FOREIGN PATENT DOCUMENTS
JP 2-152940 6/1990
WO WO 00/53563 * 9/2000

* cited by examiner

*Primary Examiner*—D. Margaret Seaman
*Assistant Examiner*—Nizal S Chandrakumar
(74) *Attorney, Agent, or Firm*—Cantor Colburn LLP

(57) ABSTRACT

Ascochlorin or an analog or derivative thereof and a compound having a primary amino group are mixed and reacted with each other in the presence/absence of a basic catalyst to synthesize a novel imino compound. The novel imino compound thus synthesized is a ligand capable of activating nuclear receptor superfamily such as retinoid orphan receptor (RXR), peroxisome proliferator-activated receptor (PPAR) and steroid receptor (PXR), and shows an effect of promoting the transcription of a drug-metabolizing enzyme CYP7A1. The imino compound has a therapeutic effect on diseases such as lifestyle-related diseases, chronic inflammation and cancers.

16 Claims, 2 Drawing Sheets

TRANSCRIPTIONAL FACTOR, PROCESS FOR PRODUCING THE SAME AND USE THEREOF

TECHNICAL FIELD

The present invention relates to novel compounds obtained from a group of microbial metabolites having a terpene side chain attached at the 3-position of orcyl aldehyde and being usually called prenylphenol antibiotics, i.e., ascochlorin, cylindrochlorin, chloronectin, LLZ-1272-•, LLZ-1272-• as well as their derivatives such as 4-O-alkyl, 2-O-alkyl, 4-O-acyl, 2-O-acyl, 2,4-diO-alkyl, 2-O-acyl-4-O-alkyl and 4-O-acyl-2-O-alkyl derivatives by reacting their aromatic aldehyde group with an amino compound (e.g., an amino acid) to synthesize their corresponding imino compounds. The present invention also relates to such a synthesis method as mentioned above. The method of the present invention is highly selective and the novel imino compounds synthesized by this method are effective in treating hypercholesterolemia, hypo-HDL-cholesterolemia, heart coronary arteriosclerosis, cerebrovascular disorders, hypertension, non-insulin-dependent diabetes mellitus, visceral fat syndrome (syndrome X), thyroid dysfunction, etc. These compounds are also effective in preventing insulin-dependent diabetes mellitus, in preventing restenosis of heart coronary arteries dilated with balloon catheters or stents, and in preventing transplanted cells, tissues and the like from being killed in regenerative medicine.

BACKGROUND ART

In 1968, Tamura, Ando and Suzuki et al. isolated novel metabolites from Hyphomycetes *Ascochyta viciae Libert* during screening of antiviral antibiotics and named them ascochlorin (Tamura et al. J. Antibiotics 21: 539-544, 1968). The absolute structure of ascochlorin has been determined as 3-[5-[1(R),2(S),6(S)-trimethyl-3-oxocyclohexyl]-3-methyl-2,4-pentadienyl]-2,4-dihydroxy-5-chloro-6-methylbenzaldehyde by the research group including one of the inventors (Ando) (Nawata Y. et al. J. Antibiotics 22: 1969). This substance was found to be identical to the fungus *Fusarium* sp. metabolite LLZ-1272-C, for which the United States Lederle Laboratories obtained a patent (U.S. Pat. No. 3,546,073, Dec. 8, 1970). Moreover, ascochlorin was found to be identical to the compound, for which Imperial Chemical Industries Ltd. (ICI) filed a patent application on Oct. 23, 1968 under GB Patent Application No. 50354/68 and filed an additional patent application on Apr. 12, 1972 in response to the structure determination of this unknown compound. However, the inventors of the present invention had already filed a Japanese patent application in March 1968 and elucidated the absolute structure of the compound in 1969 by X-ray diffraction techniques using intramolecular introduction of iodo atoms. For this reason, the designation "ascochlorin" is now accepted as a common name.

On the other hand, a carcinogenesis process in which a carcinogenic protein Ras was farnesylated in the cytoplasm and migrated to the cell membrane to cause cell canceration was among the state-of-the-art studies on cancers in late 1980s. In 1995, during screening of Ras farnesylation inhibitors among microbial metabolites, the United States Merck & Co., Inc. found that ascochlorin and its derivatives inhibited Ras farnesylation and obtained a patent for this finding (Singh, S. B et al. US Patent 94-222773 (Merck & Co., Inc., U.S.A)). Likewise, when screening inhibitors of aromatase (a rate-determining factor for androgen biosynthesis) among microbial metabolites, Ohmura et al. isolated a strong inhibitory substance out of fungal metabolites. They reported that this aromatase-inhibiting substance was cylindrochlorin when identified (Ohmura and Takamatsu et al., Chem. Pharm. Bull. 42: 953-956, 1994). All of the above compounds are common in having a structure in which a sesquiterpene side chain is attached to the 3-position of orcyl aldehyde; the inventors of the present invention collectively refer to these compounds as prenylphenol.

Prenylphenol is characterized by showing a variety of biological activities. For example, the inventors of the present invention have shown that ascochlorin arrests animal virus growth in spite of not affecting nucleic acid and protein biosynthesis. On the other hand, researchers at the Lederle Laboratories have reported that prenylphenol not only inhibits the growth of protozoan Tetrahymena, but also lowers serum cholesterol in mice and rats. In particular, they have reported that cylindrochlorin generated by dehydrogenation of the cyclohexanone ring of ascochlorin has a stronger effect of lowering serum cholesterol.

According to the above ICI's patent, ascochlorin has not only an effect of lowering serum cholesterol, but also a strong anorectic effect on rodents. This anorectic effect is strong enough to cause half inhibition of feed intake during a 2-hour intake time in mice starved for a 48-hour period receiving a trace amount of ascochlorin by oral route 2 hours before feed intake. The ICI's patent further teaches that ascochlorin has an effect of alleviating inflammatory swelling on arthritis in rats induced by adjuvant injection into their footpads.

The inventors of the present invention have isolated an ascochlorin derivative ascofuranone and have determined its structure, thus finding that this compound has a serum cholesterol-lowering effect and an anticancer effect on rodents (Jpn. J. Pharmacol. 25: 35-39, 1975 and J. Antibiotics 35: 1547-52, 1982). They have further examined pharmacological effects provided by prenylphenol, indicating that ascofuranone and 4-O-methylascochlorin prevent hypertensive rat models from entering renal failure (Eur. J. Pharmacol. 69: 429-438, 1981). Namely, prenylphenol has been found to significantly prevent hypertension which is caused in unilaterally nephrectomized rats by administering deoxycorticosterone acetate, a kind of mineral corticoid, together with 1% salt water as drinking water. It has also been found to inhibit hypercholesterolemia resulting from elevated blood pressure and to alleviate sclerotic lesions occurring in the glomeruli. Among pharmacological effects of ascochlorin derivatives, interesting are the effects of lowering serum total cholesterol in rodents and eliminating insulin resistance in non-insulin-dependent diabetes mellitus models (Agr. Biol. Chem. 46: 2865-69, 1982; DIABETES 34: 267-274, 1985).

For this reason, many studies have been carried out to synthesize novel ascochlorin derivatives using organic chemistry procedures; major articles on these studies are as shown below. The United States Lederle Laboratories have isolated ascochlorin from *Fusarium* fungi and synthesized several derivatives during structure determination of ascochlorin (Tetrahedron, Elstad G. A. et al: Tetrahedron 25: 1323-34, 1969). Further, Safaryn et al. (Safaryn J. E. et al.: Tetrahedron 42: 2635-42, 1986) and Mori et al. (Tetrahedron 41: 3049-62, 1985 & ibid 40: 2711-20, 1984) have succeeded in making a complete synthesis of ascochlorin. On the other hand, the above-mentioned Merck & Co., Inc. has synthesized some derivatives with the aim of obtaining a farnesyl transferase inhibitor against the carcinogenic protein Ras.

DISCLOSURE OF THE INVENTION

The inventors of the present invention have found that ascochlorin and its relevant compounds separated from natural sources as well as ascochlorin derivatives in which either or both of the 2- and 4-hydroxyl groups of orcyl aldehyde are substituted with an alkyl or acyl group(s) cause activation of nuclear receptors such as RXR (retinoid X receptor), RAR (all-trans-retinoic acid receptor) and PPAR (peroxisome proliferator-activated receptor) at the cell culture level, while they regulate the expression of gene information related to various diseases at the animal level.

Based on this finding, the inventors of the present invention have completed the present invention.

Namely, the present invention provides the inventions shown in 1 to 44 below.

1. A method for synthesizing a novel imino compound, which comprises reacting an aldehyde group of a fully substituted aromatic aldehyde compound as a filamentous fungal metabolite having a sesquiterpene side chain at the 3-position or a derivative thereof with an amino group of an amino compound.

2. A method for synthesizing a novel imino compound, which comprises reacting an aldehyde group of a fully substituted aromatic aldehyde compound represented by the following formula as a filamentous fungal metabolite having a sesquiterpene side chain at the 3-position or a derivative thereof:

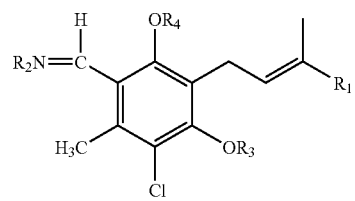

(wherein $R_1$ represents one of the following two groups:

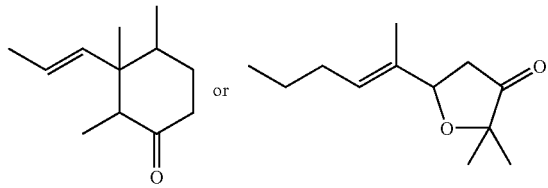

$R_3$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group, and $R_4$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group) with an amino group of an amino compound represented by the following formula:

$R_2NH_2$ (wherein $R_2$ represents $-(CH_2)_n-CHR_5R_6$ (wherein $R_5$ represents a hydrogen atom, an amino group, an amino group substituted with one or two $C_{1-6}$ alkyl groups, or a $C_{1-6}$ alkyl group substituted with phenyl, $R_6$ represents a carboxyl group, $-CONH_2$, or $-COOR_7$ (wherein $R_7$ represents a substituted or unsubstituted $C_{1-6}$ alkyl group), and n represents 0 or an integer of 1 to 6) or a residue formed by removing $NH_2$ from any amino acid) to generate the novel imino compound of the following formula:

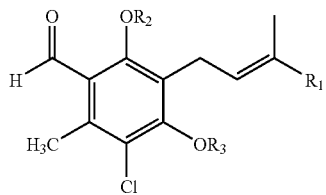

(wherein $R_1$, $R_2$, $R_3$ and $R_4$ are as defined above).

3. The method according to 1 or 2 above, wherein the fully substituted aromatic aldehyde compound is a derivative in which the hydrogen of the hydroxyl group at the 4-position is replaced with an alkyl group.

4. The method according to 1 or 2 above, wherein the fully substituted aromatic aldehyde compound is a derivative in which the hydrogen of the hydroxyl group at the 4-position is replaced with an acyl group.

5. The method according to 1 or 2 above, wherein the fully substituted aromatic aldehyde compound is a derivative in which the hydrogen of the hydroxyl group at the 2-position is replaced with an alkyl group.

6. The method according to 1 or 2 above, wherein the fully substituted aromatic aldehyde compound is a derivative in which the hydrogens of the hydroxyl groups at both the 2- and 4-positions are each replaced with an alkyl group.

7. The method according to 1 or 2 above, wherein the fully substituted aromatic aldehyde compound is a derivative in which the hydrogen of the hydroxyl group at the 2-position is replaced with an alkyl group, and the hydrogen of the hydroxyl group at the 4-position is replaced with an acyl group.

8. The method according to 1 or 2 above, wherein the fully substituted aromatic aldehyde compound is a derivative in which the hydrogen of the hydroxyl group at the 2-position is replaced with an acyl group, and the hydrogen of the hydroxyl group at the 4-position is replaced with an alkyl group.

9. The method according to any one of 1 to 8 above, wherein the fully substituted aromatic aldehyde compound is selected from ascochlorin, cylindrochlorin, ascofuranone, chloronectin, LLZ-1272-• and LLZ-1272-C•.

10. A compound of the following formula or a pharmaceutically acceptable salt or ester of the compound or optical isomers thereof:

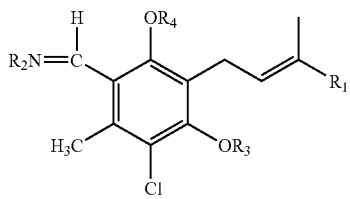

(wherein
R₁ represents one of the following two groups:

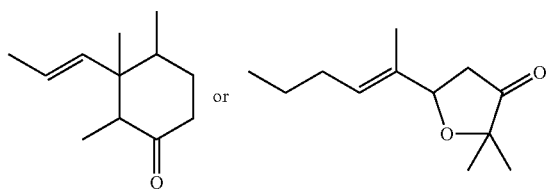

R₂ represents —(CH₂)$_n$—CHR₅R₆ (wherein R₅ represents a hydrogen atom, an amino group, an amino group substituted with one or two $C_{1-6}$ alkyl groups, or a $C_{1-6}$ alkyl group substituted with phenyl, R₆ represents a carboxyl group, —CONH₂, or —COOR₇ (wherein R₇ represents a substituted or unsubstituted $C_{1-6}$ alkyl group), and n represents 0 or an integer of 1 to 6) or a residue formed by removing NH₂ from any amino acid, R₃ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group, and R₄ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group).

11. The compound according to 10 above, wherein R₄ is a substituted or unsubstituted $C_{1-6}$ alkyl group, or a pharmaceutically acceptable salt or ester of the compound or optical isomers thereof.

12. The compound according to 10 above, wherein R₄ is an acyl group, or a pharmaceutically acceptable salt or ester of the compound or optical isomers thereof.

13. The compound according to 10 above, wherein R₃ is a substituted or unsubstituted $C_{1-6}$ alkyl group, or a pharmaceutically acceptable salt or ester of the compound or optical isomers thereof.

14. The compound according to 10 above, wherein R₃ and R₄, which may be the same or different, are each a substituted or unsubstituted $C_{1-6}$ alkyl group, or a pharmaceutically acceptable salt or ester of the compound or optical isomers thereof.

15. The compound according to 10 above, wherein R₃ is a substituted or unsubstituted $C_{1-6}$ alkyl group and R₄ is an acyl group, or a pharmaceutically acceptable salt or ester of the compound or optical isomers thereof.

16. The compound according to 10 above, wherein R₃ is an acyl group and R₄ is a substituted or unsubstituted $C_{1-6}$ alkyl group, or a pharmaceutically acceptable salt or ester of the compound or optical isomers thereof.

17. A pharmaceutical composition which comprises one or more members of a compound of the following formula or a pharmaceutically acceptable salt or ester of the compound or optical isomers thereof, as well as a pharmaceutically acceptable additive including a carrier and a diluent:

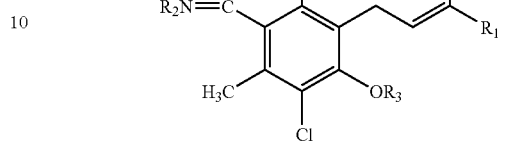

(wherein
R₁ represents one of the following two groups:

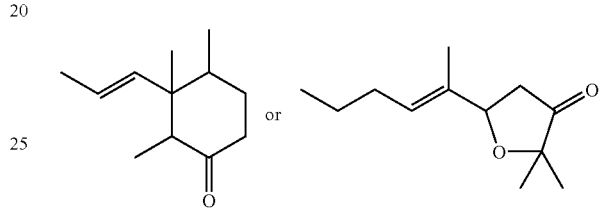

R₂ represents —(CH₂)$_n$—CHR₅R₆ (wherein R₅ represents a hydrogen atom, an amino group, an amino group substituted with one or two $C_{1-6}$ alkyl groups, or a $C_{1-6}$ alkyl group substituted with phenyl, R₆ represents a carboxyl group, —CONH₂, or —COOR₇ (wherein R₇ represents a substituted or unsubstituted $C_{1-6}$ alkyl group), and n represents 0 or an integer of 1 to 6) or a residue formed by removing NH₂ from any amino acid, R₃ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group, and R₄ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group).

18. A therapeutic or prophylactic agent for diabetes, which comprises one or more members of the compound according to any one of 10 to 16 above or a pharmaceutically acceptable salt or ester of the compound or optical isomers thereof as active ingredients.

19. A therapeutic agent for arteriosclerosis, which comprises one or more members of the compound according to any one of 10 to 16 above or a pharmaceutically acceptable salt or ester of the compound or optical isomers thereof as active ingredients.

20. A serum cholesterol-lowering agent, which comprises one or more members of the compound according to any one of 10 to 16 above or a pharmaceutically acceptable salt or ester of the compound or optical isomers thereof as active ingredients.

21. A therapeutic agent for multiple risk factor syndrome, which comprises one or more members of the compound according to any one of 10 to 16 above or a pharmaceutically acceptable salt or ester of the compound or optical isomers thereof as active ingredients.

22. A therapeutic agent for hypertension, which comprises one or more members of the compound according to any one of 10 to 16 above or a pharmaceutically acceptable salt or ester of the compound or optical isomers thereof as active ingredients.

23. A therapeutic agent for myxedema, which comprises one or more members of the compound according to any one of 10 to 16 above or a pharmaceutically acceptable salt or ester of the compound or optical isomers thereof as active ingredients.

24. An antiphlogistic for treating chronic inflammation, which comprises one or more members of the compound according to any one of 10 to 16 above or a pharmaceutically acceptable salt or ester of the compound or optical isomers thereof as active ingredients.

25. A prophylactic or therapeutic agent for restenosis of arterial lumen dilated with a balloon catheter or stent, which comprises one or more members of the compound according to any one of 10 to 16 above or a pharmaceutically acceptable salt or ester of the compound or optical isomers thereof as active ingredients.

26. A survival promoter for ensuring survival of cells or tissues differentiated and induced from stem cells to be transplanted to a recipient in regenerative medicine, which comprises one or more members of the compound according to any one of 10 to 16 above or a pharmaceutically acceptable salt or ester of the compound or optical isomers thereof as active ingredients.

27. A method for treating or preventing diabetes, which comprises administering to a patient a therapeutically or prophylactically effective amount of one or more members of the compound according to any one of 10 to 16 above or a pharmaceutically acceptable salt or ester of the compound or optical isomers thereof.

28. A method for treating arteriosclerosis, which comprises administering to a patient a therapeutically effective amount of one or more members of the compound according to any one of 10 to 16 above or a pharmaceutically acceptable salt or ester of the compound or optical isomers thereof.

29. A method for lowering serum cholesterol, which comprises administering to a patient a therapeutically or prophylactically effective amount of one or more members of the compound according to any one of 10 to 16 above or a pharmaceutically acceptable salt or ester of the compound or optical isomers thereof.

30. A method for treating multiple risk factor syndrome, which comprises administering to a patient a therapeutically effective amount of one or more members of the compound according to any one of 10 to 16 above or a pharmaceutically acceptable salt or ester of the compound or optical isomers thereof.

31. A method for treating hypertension, which comprises administering to a patient a therapeutically effective amount of one or more members of the compound according to any one of 10 to 16 above or a pharmaceutically acceptable salt or ester of the compound or optical isomers thereof.

32. A method for treating myxedema, which comprises administering to a patient a therapeutically effective amount of one or more members of the compound according to any one of 10 to 16 above or a pharmaceutically acceptable salt or ester of the compound or optical isomers thereof.

33. A method for treating chronic inflammation, which comprises administering to a patient a therapeutically effective amount of one or more members of the compound according to any one of 10 to 16 above or a pharmaceutically acceptable salt or ester of the compound or optical isomers thereof.

34. A method for preventing or treating restenosis of arterial lumen dilated with a balloon catheter or stent, which comprises administering to a patient a therapeutically or prophylactically effective amount of one or more members of the compound according to any one of 10 to 16 above or a pharmaceutically acceptable salt or ester of the compound or optical isomers thereof.

35. A method for ensuring survival of cells or tissues differentiated and induced from stem cells to be transplanted to a recipient in regenerative medicine, which comprises administering to a recipient an effective amount of one or more members of the compound according to any one of 10 to 16 above or a pharmaceutically acceptable salt or ester of the compound or optical isomers thereof.

36. The use of the compound according to any one of 10 to 16 above or a pharmaceutically acceptable salt or ester of the compound or optical isomers thereof for the manufacture of a therapeutic or prophylactic agent for diabetes.

37. The use of the compound according to any one of 10 to 16 above or a pharmaceutically acceptable salt or ester of the compound or optical isomers thereof for the manufacture of a therapeutic agent for arteriosclerosis.

38. The use of the compound according to any one of 10 to 16 above or a pharmaceutically acceptable salt or ester of the compound or optical isomers thereof for the manufacture of a serum cholesterol-lowering agent.

39. The use of the compound according to any one of 10 to 16 above or a pharmaceutically acceptable salt or ester of the compound or optical isomers thereof for the manufacture of a therapeutic agent for multiple risk factor syndrome.

40. The use of the compound according to any one of 10 to 16 above or a pharmaceutically acceptable salt or ester of the compound or optical isomers thereof for the manufacture of a therapeutic agent for hypertension.

41. The use of the compound according to any one of 10 to 16 above or a pharmaceutically acceptable salt or ester of the compound or optical isomers thereof for the manufacture of a therapeutic agent for myxedema.

42. The use of the compound according to any one of 10 to 16 above or a pharmaceutically acceptable salt or ester of the compound or optical isomers thereof for the manufacture of an antiphlogistic for treating chronic inflammation.

43. The use of the compound according to any one of 10 to 16 above or a pharmaceutically acceptable salt or ester of the compound or optical isomers thereof for the manufacture of a prophylactic or therapeutic agent for restenosis of arterial lumen dilated with a balloon catheter or stent.

44. The use of the compound according to any one of 10 to 16 above or a pharmaceutically acceptable salt or ester of the compound or optical isomers thereof for the manufacture of a survival promoter for ensuring survival of cells or tissues differentiated and induced from stem cells to be transplanted to a recipient in regenerative medicine.

BEST MODE FOR CARRYING OUT THE INVENTION

Figure 1:
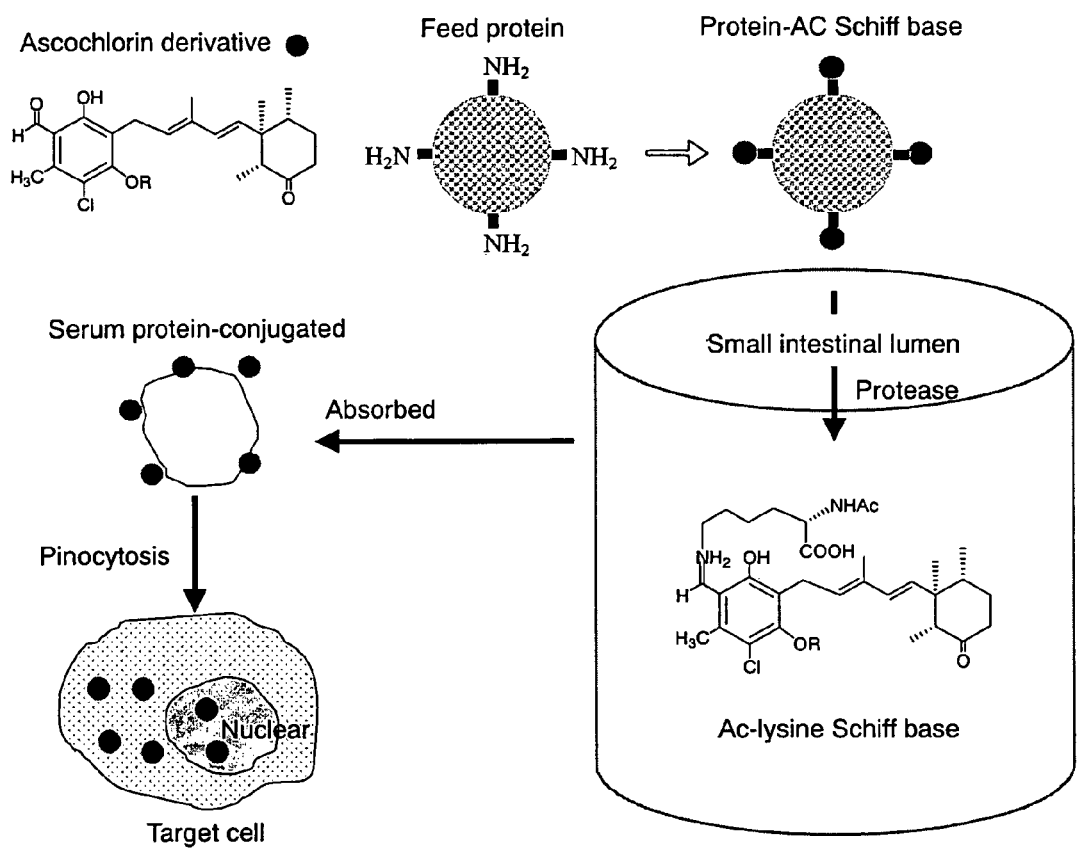
FIG. 1 is a schematic view of the mechanism whereby target cells are affected by an ascochlorin-lysine Schiff base formed in the small intestinal lumen from lysine and an ascochlorin derivative attached to feed protein.

As used herein, the phrase "fully substituted aromatic aldehyde compound as a filamentous fungal metabolite having a sesquiterpene side chain at the 3-position or a derivative thereof" is intended to mean a compound of the following formula:

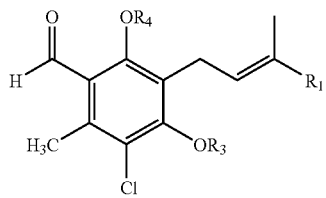

(wherein $R_1$ represents one of the following two groups:

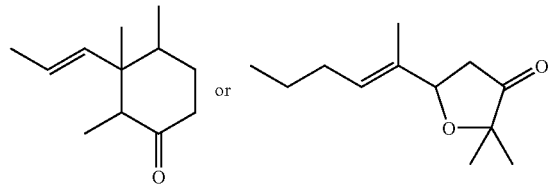

$R_3$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group, and $R_4$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group).

The numbering of carbon atoms on the benzene ring is made as follows: the 1-position is given to the carbon atom attached to the aldehyde group, followed by the 2-, 3- to 6-positions in a clockwise direction.

As used herein, the term "$C_{1-6}$ alkyl group" means a linear or branched $C_{1-6}$ alkyl group. Examples of a $C_{1-6}$ alkyl group include methyl, ethyl, n-propyl, i-propyl, n-butyl, i-butyl, t-butyl, n-pentyl and n-hexyl. Such a "$C_{1-6}$ alkyl group" may have one or more substituents selected from, for example, hydroxy, amino, carboxyl, nitro, an aryl group, a substituted aryl group, mono- or lower alkylamino (e.g., mono- or di-$C_{1-6}$ alkylamino such as methylamino, ethylamino, propylamino, dimethylamino or diethylamino), alkoxy (e.g., $C_{1-6}$ alkoxy such as methoxy, ethoxy, propoxy or hexyloxy), alkylcarbonyloxy (e.g., $C_{1-6}$ alkyl-carbonyloxy such as acetoxy or ethylcarbonyloxy) or a halogen atom.

As used herein, the term "$C_{2-6}$ alkenyl group" means a linear or branched $C_{2-6}$ alkenyl group. Examples of a $C_{2-6}$ alkenyl group available for use include vinyl, allyl, 2-methylallyl, i-propenyl, 2-butenyl, 3-butenyl, 2-pentenyl, 3-pentenyl, 2-hexenyl and 3-hexenyl. Such a "$C_{2-6}$ alkenyl group" may have one or more substituents selected from, for example, hydroxy, amino, carboxyl, nitro, mono- or di-alkylamino (e.g., mono- or di-$C_{1-6}$ alkylamino such as methylamino, ethylamino, propylamino, dimethylamino or diethylamino), alkoxy (e.g., $C_{1-6}$ alkoxy such as methoxy, ethoxy, propoxy or hexyloxy), alkylcarbonyloxy (e.g., $C_{1-6}$ alkylcarbonyloxy such as acetoxy or ethylcarbonyloxy) or a halogen atom.

As used herein, the term "$C_{2-6}$ alkynyl group" means, for example, a linear or branched $C_{2-6}$ alkynyl group. Examples of a $C_{2-6}$ alkynyl group available for use include ethynyl, 2-propynyl, 2-butynyl, 3-butynyl, 2-pentynyl, 3-pentynyl, 2-hexynyl and 3-hexynyl. Such a "$C_{2-6}$ alkynyl group" may have one or more substituents selected from, for example, hydroxy, amino, carboxyl, nitro, mono- or di-alkylamino (e.g., mono- or di-$C_{1-6}$ alkylamino such as methylamino, ethylamino, propylamino, dimethylamino or diethylamino), alkoxy (e.g., $C_{1-6}$ alkoxy such as methoxy, ethoxy, propoxy or hexyloxy), alkylcarbonyloxy (e.g., $C_{1-6}$ alkyl-carbonyloxy such as acetoxy or ethylcarbonyloxy) or a halogen atom.

As used herein, the term "$C_{3-8}$ cycloalkyl group" is intended as a cyclopropyl group, a cyclobutyl group, a cyclopentyl group, a cyclohexyl group, cyclooctyl group, etc. Such a "cycloalkyl group" may have one or more substituents selected from, for example, hydroxy, amino, carboxyl, nitro, mono- or di-alkylamino (e.g., mono- or di-$C_{1-6}$ alkylamino such as methylamino, ethylamino, propylamino, dimethylamino or diethylamino), alkoxy (e.g., $C_{1-6}$ alkoxy such as methoxy, ethoxy, propoxy or hexyloxy), alkylcarbonyloxy (e.g., $C_{1-6}$ alkyl-carbonyloxy such as acetoxy or ethylcarbonyloxy) or a halogen atom.

In a case where $R_2$ represents a residue formed by removing $NH_2$ from any amino acid, examples of any amino acid intended herein include lysine, hydroxylysine, arginine, glycine, alanine, valine, leucine, isoleucine, serine, threonine, aspartic acid, glutamic acid, asparagine, glutamine, cysteine, cystine, methionine, phenylalanine, tyrosine, tryptophan, histidine, proline, β-alanine, γ-aminobutyric acid, homocysteine, ornithine, 5-hydroxytryptophan, 3,4-dihydroxyphenylalanine, triiodothyronine and thyroxine.

As used herein, the term "acyl group" means a group represented by —COR (wherein R represents any one of a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, and a monocyclic or polycyclic aromatic or heterocyclic ring). Such an "acyl group" and an "acylamino group" may each have one or more substituents selected from, for example, hydroxy, amino, carboxyl, nitro, mono- or di-alkylamino (e.g., mono- or di-$C_{1-6}$ alkylamino such as methylamino, ethylamino, propylamino, dimethylamino or diethylamino), alkoxy (e.g., $C_{1-6}$ alkoxy such as methoxy, ethoxy, propoxy or hexyloxy), alkylcarbonyloxy (e.g., $C_{1-6}$ alkyl-carbonyloxy such as acetoxy or ethylcarbonyloxy) or a halogen atom; and such a substituent means a substituent located on R.

As used herein, the term "aryl group" means an atomic group left by removing one hydrogen atom from an aromatic hydrocarbon. Particularly preferred is a $C_{6-14}$ aryl group. Examples of a $C_{6-14}$ aryl group available for use include phenyl, naphthyl, tolyl, xylyl, biphenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-azulenyl, 2-azulenyl, 4-azulenyl, 5-azulenyl and 6-azulenyl. Such an "aromatic ring" may have one or more substituents selected from, for example, lower alkyl, hydroxy, amino, carboxyl, nitro, mono- or di-lower alkylamino (e.g., mono- or di-$C_{1-6}$ alkylamino such as methylamino, ethylamino, propy lamino, dimethylamino or diethylamino), lower alkoxy (e.g., $C_{1-6}$ alkoxy such as methoxy, ethoxy, propoxy or hexyloxy), lower alkylcarbonyloxy (e.g., $C_{1-6}$ alkyl-carbonyloxy such as acetoxy or ethylcarbonyloxy), trihalomethane, trihalomethoxy, a halogen atom or aryl such as phenyl.

ing the hydrogen of the hydroxyl group at the 4-position with —$CH_2COOH$ can be dissolved in water in an amount of 6% or more in the small intestine (pH 7.2 to 7.4); this derivative will be rapidly absorbed and hence is likely to show toxicity when orally administered.

TABLE 1

Comparison on activity between in-feed administration and forced oral administration

| | Compound | Spraying of acetone solution | Mechanical mixing | Forced oral administration |
|---|---|---|---|---|
| Decrease in serum cholesterol levels (n = 6), tested in triplicate | 1 | 15.2%-25.1% decrease, P < 0.01 in all three tests Serum is vivid yellow. | No decrease in all three tests Serum is not colored. | No decrease in all three tests Serum is not colored. |
| | 2 | 17.5%-22.7% decrease, P < 0.01 in all three tests Serum is yellow. | 14.8%, P < 0.05 8.2%, ns 7.2%, ns | 4.8%, ns 10.9%, ns 8.8%, ns |
| % Reduction of urinary sugar excretion (n = 4), tested in triplicate | 1 | Urinary sugar excretion is reduced; 98.5%, 97.3% and 99.0%, P < 0.01 in all three tests | No inhibitory effect is observed against urinary sugar excretion in all three tests | No inhibitory effect is observed against urinary sugar excretion in all three tests |
| | 2 | Urinary sugar excretion is reduced; 99.2%, 97.6% and 98.0%, P < 0.01 in all three tests | Urinary sugar excretion is reduced; 52.1%, P < 0.05, 38.5% (ns) and 41.8% P < 0.05 Feed intake is reduced and body weight gain is inhibited. | Toxic death; 2/4 in the first test 1/4 in the second test 1/4 in the third test Not effective |

Note 1)
All data were analyzed by Student's paired t-test using a drug-untreated group as a control.
Note 2)
Effect on serum total cholesterol: Male ICR mice (5 weeks of age) were administered with a drug for 1 week, followed by blood collection from the heart to determine the level of serum cholesterol for each mouse by the Zurkowski method.
Note 3)
Urinary sugar excretion: db/db mice (6-7 weeks of age, male 2, female 2) were housed in a rat cage for urine collection and administered with a drug. Urine was collected every day, and the amount of urine and the concentration of urinary sugar were measured to calculate the level of urinary sugar excretion per animal.

As intended herein, a particularly preferred salt is a pharmaceutically acceptable acid addition salt. Examples of such a salt available for use include those with inorganic acids (e.g., hydrochloric acid, phosphoric acid, hydrobromic acid, sulfuric acid), those with organic acids (e.g., acetic acid, formic acid, propionic acid, fumaric acid, maleic acid, succinic acid, tartaric acid, lactic acid, citric acid, malic acid, oxalic acid, benzoic acid, methanesulfonic acid, p-toluenesulfonic acid, benzenesulfonic acid) or those with alkalis (e.g., sodium, potassium, magnesium, calcium, ammonium, pyridine, triethylamine).

As intended herein, a particularly preferred ester is an alkyl ester (e.g., methyl ester, ethyl ester, n-propyl ester, i-propyl ester) of a carboxyl group, if any.

The Schiff base (imino compound) of the present invention also encompasses all stereoisomers and optical isomers.

Ascochlorin and 4-O-methylascochlorin having a methylated hydroxyl group at the 4-position (Compound-1) are both fat-soluble and substantially insoluble in water. Since single molecules of these compounds are released and dissolved at a very slow rate from their crystal lattices into water, most of them pass through the digestive tract without being absorbed when orally administered to small animals (e.g., rats, mice) in the fasting state. In addition to low bioavailability, their effectiveness will be affected by the presence or absence of dietary intake (Agr. Biol. Chem. 46: 775-781, 1982). Poor reproducibility in animal experiments has constituted a serious obstacle to the practical use of these compounds.

The rate of releasing and dissolving single molecules from crystal lattices into water can be increased by intramolecular introduction of a polar group. In fact, 4-O-carboxymethylascochlorin (Compound-2) derived from ascochlorin by replac- In contrast, the solubility of Compound-1 in water is as extremely low as about 0.7 g/l; Compounds-1 and -2 are poles apart in terms of solubility in water. Interestingly, when dissolved in acetone and sprayed over feed in an amount of 0.1% for uniform penetration before being given to mice, both ascochlorin derivatives exert substantially equal effects in lowering serum total cholesterol (in normal mice) and inhibiting urinary sugar excretion (in genetically obese diabetic mice, C57BL/ksj db/db) (Table 1). However, even when both compounds are simply mixed in a mechanical manner into feed in an amount of 0.1% or even when both compounds are given for forced oral administration in the same drug amount calculated from feed intake, there is no reproducibility in their efficacy unlike the case where their acetone solutions are sprayed over feed. In particular, the water-insoluble Compound-1 shows little efficacy unless it is dissolved in acetone and sprayed over feed.

The fact that in spite of such a large difference in water solubility, both compounds show substantially equal pharmacological effects when dissolved in acetone, sprayed over feed and air-dried before being given to animals suggests the presence of some interaction between drug and feed. Then, an attempt was made to collect each compound from feed sprayed with the drug dissolved in acetone or feed prepared by mechanical mixing with each drug powder. Each feed was allowed to stand overnight at room temperature and then extracted with 20 volumes of acetone to collect each compound (Table 2).

TABLE 2

Collection experiment of Compounds-1 and -2 dissolved in acetone and sprayed over feed

| | Feed sprayed with acetone solution (air-dried) | | Feed prepared by mechanical mixing with drug | | |
|---|---|---|---|---|---|
| | Extraction time | Recovery rate (%) | Extraction solvent | Extraction time | Recovery rate (%) |
| Compound-1 | 1 hour | 0 | Compound-1 | 1 hour | 86 |
| | 6 hours | 0 | | 6 hours | 90 |
| | 16 hours | 0 | | 16 hours | 85 |
| Compound-2 | 1 hour | 0 | Compound-2 | 1 hour | 91 |
| | 6 hours | 0 | | 6 hours | 90 |
| | 16 hours | 0 | | 16 hours | 76 |

Compounds-1 and -2 in the extracts were quantified by HPLC.
Extraction conditions: room temperature As shown in Table 2, in a case where both compounds are respectively dissolved in acetone, sprayed over feed and then air-dried, they are not extracted at all even after being immersed and extracted in acetone for 16 hours. However, in a case where both compounds are respectively mixed in a mechanical manner into feed powder, they are extracted, upon addition of acetone, into the solvent independently of the extraction time. This fact suggests that when acetone solutions of both compounds are sprayed over feed powder, these compounds cause chemical reaction with some component in the feed to form covalent bonding.

Next, feed powder which had been sprayed with an acetone solution of each compound and then air-dried was added to an organic solvent supplemented with an acid (e.g., acetic acid, hydrochloric acid) and sampled over time to quantify each compound released into the solvent. As shown in Table 3, when each feed was immersed in the acidic organic solvent, the amount of each compound released from the feed was increased with the passage of time. This fact means that Compounds-1 and -2, when dissolved in acetone and sprayed over feed, form covalent bonds with a feed component(s) simultaneously with evaporation of acetone, while such covalent bonds are hydrolyzed upon addition of an acid. This reaction is an extremely rare reaction occurring between solid phase and liquid layer. As a similar reaction, the "aminocarbonyl reaction" can be presented which is observed in foods containing a mixture of proteins and reducing carbohydrates. However, such a reaction between protein and reducing carbohydrate proceeds in an irreversible manner and finally provides a brown substance, whereas the reaction between prenylphenol and feed protein is characterized by its reversibility.

TABLE 3

Release of both compounds from feed in acidic organic solvent

| | | Recovery rate (%) | | | |
|---|---|---|---|---|---|
| Acidic organic solvent | Compound | 0 hours | 1 hour | 8 hours | 16 hours |
| 5% Acetic acid-containing ethanol | Compound-1 | 10.2 | 33.9 | 65.0 | 81.7 |
| | Compound-2 | 8.6 | 41.3 | 71.3 | 79.5 |
| 5% Hydrochloric acid-containing methanol | Compound-1 | 40.0 | 80.4 | 92.1 | 97.4 |
| | Compound-2 | 53.2 | 84.2 | 99.6 | 100.4 |

Compounds-1 and -2 in the extracts were quantified by HPLC and compared with their initial amounts to calculate the recovery rate.

Ascochlorin compounds are characterized by having an aromatic aldehyde group and a 6-membered cyclic ketone side chain. They all have the possibility of forming an imino compound with the ω-amino group of a protein lysine residue. Then, glycine ethyl ester and glycine amide were selected as model compounds and mixed with ascochlorin, ascofuranone, Compound-1 or Compound-2 in an organic solvent in the presence of triethanolamine. Upon mixing, each solution immediately turned yellow, which was indicative of the formation of a new compound. When the reaction solutions were developed on silica gel thin-layer chromatography, the spots corresponding to ascochlorin, ascofuranone, Compound-1 and Compound-2 were found to disappear and instead new yellow spots were found to appear. Moreover, when the reaction solutions were concentrated and applied to silica gel column chromatography, yellow substances could be isolated in pure form. Ascochlorin and Compound-1 are fat-soluble and easily dissolved in chloroform, ethyl acetate or the like, but are difficult to dissolve in methanol. In contrast, the yellow substances formed upon mixing with glycine ethyl ester or glycine amide are insoluble in a low polar solvent such as chloroform or benzene, but are soluble in methanol. They can also be dissolved in water to some extent although their original compounds are not dissolved in water at all. In a case where an ascochlorin or ascofuranone compound is used as prenylphenol for use in producing the compound of the present invention, the following compounds can be presented as examples.

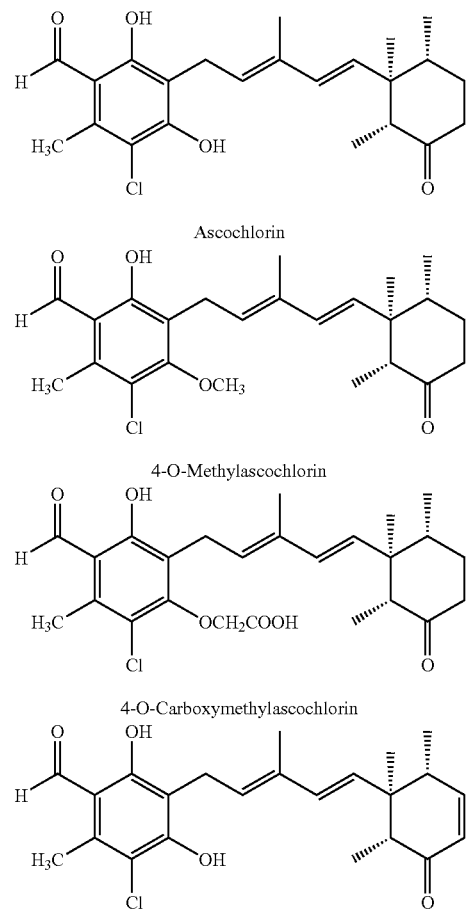

Ascochlorin

4-O-Methylascochlorin

4-O-Carboxymethylascochlorin

Cylindrochlorin

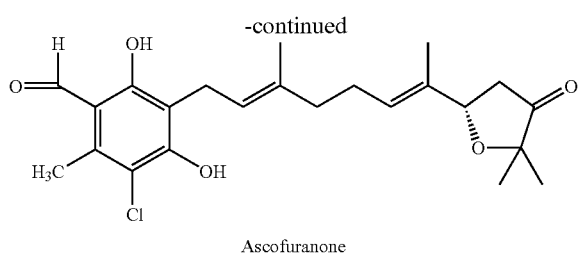

Ascofuranone

The structures of yellow substances formed by reaction between prenylphenols and primary amino compounds were elucidated by infrared absorption spectra and NMR spectra. When analyzing the NMR spectra, the proton of aldehyde was found to disappear and instead an amino proton was found to appear. The infrared absorption spectra proved that a primary amino compound is attached to the aldehyde group, but not to ketone in the cyclohexanone ring because the carbonyl absorption band of the aldehyde group disappeared simultaneously with the appearance of a stretching vibration band of —C=H—. Namely, prenylphenol and glycine amide are reacted as shown in [Reaction Scheme 1] below and, moreover, this reaction is reversible.

[Reaction Scheme 1]

Reaction between glycine amide and ascochlorin derivative

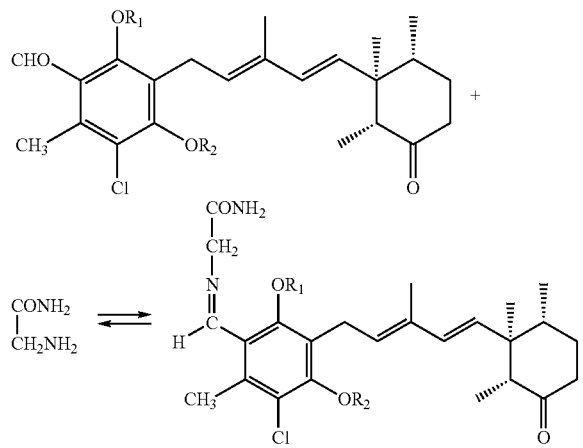

As long as it has a primary amino group, any compound can achieve the above reaction without exceptions. In particular, protein-constituting amino acids are preferred as materials for synthesis of imino compounds. It is certainly an imino compound-forming reaction that occurs when prenylphenol is dissolved in acetone and sprayed over feed. Feed proteins covalently attached to prenylphenol will be hydrolyzed in the small intestine by the action of proteases. Finally, a lysine residue having prenylphenol attached at the ω-position or an oligopeptide containing such a lysine residue will be readily absorbed from the digestive tract because of its increased dissolution rate in water when compared to ascochlorin or Compound-1.

In contrast, a rapidly absorbable prenylphenol like Compound-2 is covalently attached to the ω-amino group of a protein lysine residue and, as a result of feed protein hydrolysis, produces a lysine residue having prenylphenol attached at the ω-position or an oligopeptide containing such a lysine residue, thus slowing its absorption into the small intestine. In this case, Compound-2 is therefore prevented from being absorbed at once and in a large amount compared to simple administration of Compound-2, so that toxicity is less likely to occur. Although the effect of Compound-2 is time-dependent, Compound-2 will continue to be maintained at an effective blood level, which leads to increased efficacy. The interaction between ascochlorin or its derivative and feed protein is as shown in FIG. 1.

An example will be given below to illustrate how to synthesize the Schiff base (imino compound) of the present invention.

1. Ascochlorin Compounds for Use as Starting Materials

As starting materials for synthesis of ascochlorin derivatives, the above-listed ascochlorin (AC), 4-O-methylascochlorin (MAC), 4-carboxymethylascochlorin (AS-6) and ascofuranone (AF) were used.

2. Synthesis of Acetylascochlorin Compounds

<Synthesis>

The ascochlorin compounds (AC, MAC, AS-6, AF) were acylated with acetic anhydride/pyridine, extracted with ethyl acetate, washed with diluted hydrochloric acid and saturated aqueous sodium bicarbonate, and then concentrated to give crude acetylascochlorin compounds.

The 2-O-, 4-O-diacetyl form was further partially hydrolyzed in triethylamine/aqueous THF to give a 4-O-monoacetyl form. The resulting acetylascochlorin compounds are shown below.

<Acetylascochlorin Compounds>

| No. | Abbreviation | Structural formula |
|---|---|---|
| 22 | diAcAC | 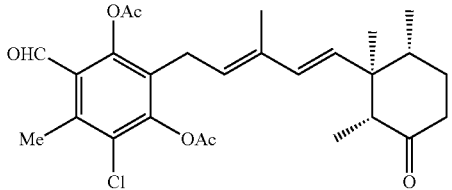 |

-continued

| No. | Abbreviation | Structural formula |
|---|---|---|
| 34 | AcAC | (structure with OH, OHC, Me, Cl, OAc on aromatic ring, linked to cyclohexanone) |
| 36, 37 | AcAC | (structure with OH, OHC, Me, Cl, OAc on aromatic ring, linked to cyclohexanone) |
| 43 | AcMAC | (structure with OAc, OHC, Me, Cl, OMe on aromatic ring, linked to cyclohexanone) |
| 45 | diAcAF | (structure with OAc, OHC, Me, Cl, OAc on aromatic ring, linked to dimethyl lactone) |

<TLC, IR, NMR>

TLC (thin-layer chromatography), IR and NMR data of the above acetylascochlorin compounds are summarized in the tables shown later.

3. Synthesis of Schiff Bases of Acetylascochlorin Compounds

<Synthesis>

The ascochlorin compounds (starting materials) or the acetylascochlorin compounds prepared above were condensed with amino acid derivatives having a primary amine in the presence or absence of a base (e.g., triethylamine, potassium carbonate) and in a solvent (e.g., methanol, THF).

After confirming the progress of condensation (i.e., the appearance of band yellow spots as a result of the formation of Schiff bases) by TLC, the Schiff bases were extracted from the reaction solutions and then evaporated to remove the solvent, or alternatively, the reaction solvent was directly distilled off under reduced pressure. In this way, concentrates containing the Schiff bases were obtained.

After concentration, silica gel column chromatography was performed to isolate the Schiff bases.

As shown in the list below, each Schiff base had a structure concentrated between the salicylaldehyde site and the primary amine.

<Schiff Bases of AC>

(General structure: R-CH=N- attached to aromatic ring with OH, Me, Cl, OH substituents, linked via isoprenoid chain to cyclohexanone)

| No. | Abbreviation | R |
|---|---|---|
| 5, 7 | AC + LysOH | =N–(CH$_2$)$_4$–CH(NH$_2$)–CO$_2$H |
| 6, 8 | AC + GlyOMe | =N–CH$_2$–CO$_2$Me |
| 9 | AC + GlyOH | =N–CH$_2$–CO$_2$H |
| 13 | AC + GlyNH$_2$ | =N–CH$_2$–CONH$_2$ |

-continued

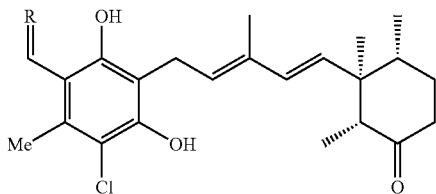

| No. | Abbreviation | R |
|---|---|---|
| 16 | AC + NAcLysOH | 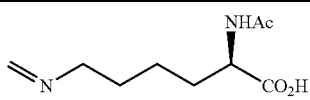 |
| 31 | AC + âAlaNH$_2$ | 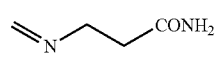 |
| 41 | AC + PheNH$_2$ | 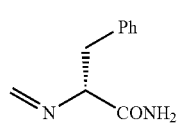 |

AC (Ascochlorin, R: =O)

<Schiff Bases of MAC>

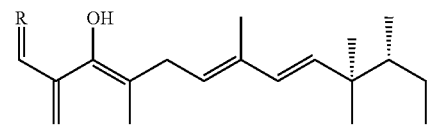

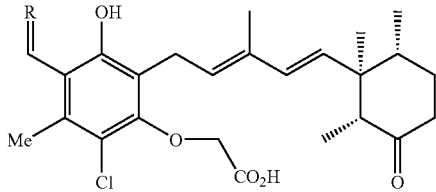

| No. | Abbreviation | R |
|---|---|---|
| 17 | AS-6 + GlyNH$_2$ |  |
| 18 | AS-6 + GlyOMe | 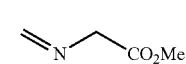 |
| 19 | AS-6 + NAcLysOH | 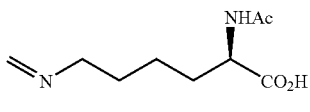 |
| 30 | AS-6 + âAlaNH$_2$ | 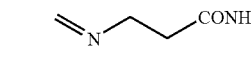 |
| 28 | MAC + Orn | 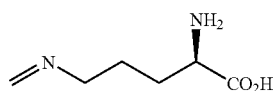 |
| 40 | MAC + PheNH$_2$ | 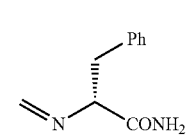 |

-continued

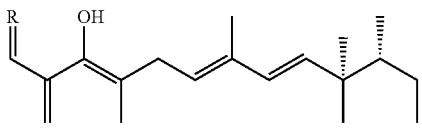

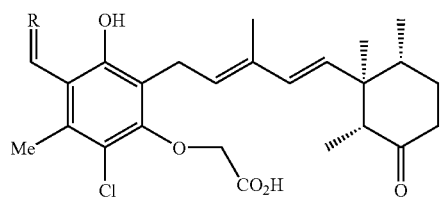

| No. | Abbreviation | R |
|---|---|---|
| 42 | MAC + AlaNH$_2$ | 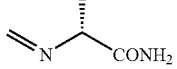 |

AS-6(4-O-Carboxymethylascochlorin, R: =O)

<Schiff Bases of AS-6>
<Schiff Bases of AF>

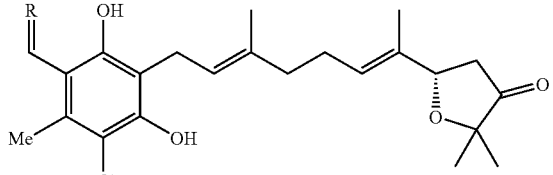

| No. | Abbreviation | R |
|---|---|---|
| 15 | AF + GlyNH$_2$ | 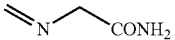 |

AF(Ascofuranon, R: =O)

<Schiff Bases of AcAC>

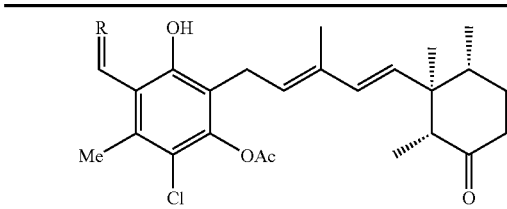

| No. | Abbreviation | R |
|---|---|---|
| 23 | AcAC + GlyNH$_2$ | 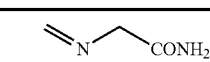 |
| 26 | AcAC + GlyOMe | 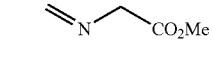 |
| 27 | AcAC + âAlaNH$_2$ | 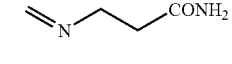 |

-continued

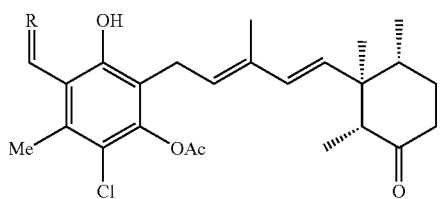

| No. | Abbreviation | R |
|---|---|---|
| 37 | AcAC + âAlaNH₂ | =N-CH₂CH₂-CONH₂ |
| 39 | AcAC + PheNH₂ | =N-CH(CH₂Ph)-CONH₂ |
| 44 | AcAC + AlaNH₂ | =N-CH(Me)-CONH₂ |

AcAC (Acetylascochlorin, R: =O)

<Schiff Bases of AcAF>

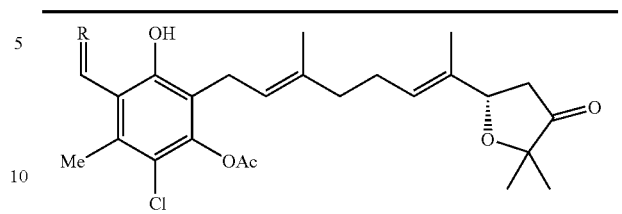

| No. | Abbreviation | R |
|---|---|---|
| 48 | AcAF + AlaNH₂ | =N-CH(Me)-CONH₂ |

AcAF(Acetylascofuranon, R: =O)

<TLC, IR, NMR>

TLC, IR and NMR data of the above acetylascochlorin compounds are summarized in the tables shown later.

4. Synthesis of Acetals of Ascochlorin Compounds

<Synthesis>

2-O-Acetylascochlorin compounds are condensed with alcohols in the presence or absence of a reaction solvent by the action of a base catalyst.

After confirming the progress of the reaction by TLC, the reaction solutions were evaporated to remove the reaction solvent and then crystallized, or alternatively, the concentrates of the reaction solutions were applied to silica gel column chromatography, thereby obtaining acetals.

<Acetals of Ascochlorin Compounds>

| No. | Abbreviation | R |
|---|---|---|
| 32 | diMeAcAC | (structure with OMe, OH, Me, Cl, OAc, cyclohexanone) |
| 35 | diEtAcAC | (structure with OEt, OH, Me, Cl, OAc, cyclohexanone) |
| 46 | diEtMAC | (structure with OEt, OH, Me, Cl, OMe, cyclohexanone) |

-continued

| No. | Abbreviation | R |
|---|---|---|
| 47 | diEtAcAF | (structure shown) |
| 49 | diBuMAC | (structure shown) |
| 50 | PGMAC | (structure shown) |

5. Silica Gel TLC Data of Ascochlorin Derivatives

To confirm the Rf values and purity of various ascochlorin derivatives, TLC analysis was performed. The results obtained are shown below.

| No. | AC compound & Schiff base | | Developing solvent | Rf value | TLC purity |
|---|---|---|---|---|---|
| 6, 8 | AC | GlyOMe | 50% AcOEt/Hexane | 0.33 | One spot |
| 10 | MAC | GlyOMe | 50% AcOEt/Hexane | 0.36 | One spot |
| 11 | MAC | GlyNH$_2$ | 5% MeOH/CHCl$_3$ | 0.53 | Slightly impure |
| 13 | AC | GlyNH$_2$ | 5% MeOH/CHCl$_3$ | 0.57 | One spot |
| 14 | MAC | NAcLysOH | 20% MeOH/CHCl$_3$ | 0.04 | Impure (decomposed?) |
| 15 | AF | GlyNH$_2$ | 10% MeOH/CHCl$_3$ | 0.54 | One spot |
| 16 | AC | NAcLysOH | 20% MeOH/CHCl$_3$ | 0.27 | One spot |
| 17 | AS-6 | GlyNH$_2$ | 20% MeOH/CHCl$_3$ | 0.41 | One spot (containing Et$_3$N) |
| 18 | AS-6 | GlyOMe | 20% MeOH/CHCl$_3$ | 0.57 | One spot |
| 22 | diAcAC | | 30% AcOEt/Hexane | 0.33 | Spot slightly above |
| 23 | AcAC | GlyNH$_2$ | 10% MeOH/CHCl$_3$ | 0.48 | Spot slightly above |
| 25 | MAC | âAlaNH$_2$ | 10% MeOH/CHCl$_3$ | 0.42 | One spot |
| 26 | AcAC | GlyOMe | 30% AcOEt/Hexane | 0.22 | Spot slightly above |
| 27 | AcAC | âAlaNH$_2$ | 10% MeOH/CHCl$_3$ | 0.42 | One spot |
| 30 | AS-6 | âAlaNH$_2$ | 30% MeOH/CHCl$_3$ | 0.58 | One spot |
| 31 | AC | âAlaNH$_2$ | 10% MeOH/CHCl$_3$ | 0.49 | One spot |
| 32 | diMeAcAC | | 30% AcOEt/Hexane | 0.38 | One spot |
| 34 | AcAC | | 30% AcOEt/Hexane | 0.46 | Substantially one spot |
| 35 | diEtAcAC | | 30% AcOEt/Hexane | 0.48 | One spot |
| 36 | AcAC | | 30% AcOEt/Hexane | 0.46 | One spot (crystalline) |
| 37 | AcAC | âAlaNH$_2$ | 10% MeOH/CHCl$_3$ | 0.42 | Alternative to No. 27. Same Rf |
| 39 | AcAC | PheNH$_2$ | 10% MeOH/CHCl$_3$ | 0.39 | Substantially one spot |
| 40 | MAC | PheNH$_2$ | 10% MeOH/CHCl$_3$ | 0.36 | Substantially one spot |
| 41 | AC | PheNH$_2$ | 10% MeOH/CHCl$_3$ | 0.28 | Substantially one spot |
| 42 | MAC | AlaNH$_2$ | 10% MeOH/CHCl$_3$ | 0.53 | One spot |
| 43 | AcMAC | | 30% AcOEt/Hexane | 0.40 | Substantially one spot |
| 44 | AcAC | AlaNH$_2$ | 10% MeOH/CHCl$_3$ | 0.62 | One spot |
| 45 | diAcAF | | 30% AcOEt/Hexane | 0.42 | Substantially one spot |
| 46 | diEtMAC | | 30% AcOEt/Hexane | 0.58 | One spot (crystallized) |
| 47 | diEtAcAF | | 20% AcOEt/Hexane | 0.33 | One spot |
| 48 | AcAF | AlaNH$_2$ | 10% MeOH/CHCl$_3$ | 0.58 | One spot |
| 49 | diBuMAC | | 20% AcOEt/Hexane | 0.45 | One spot |
| 50 | PGMAC | | 30% AcOEt/Hexane | 0.31 | One spot |

6. IR Data of Ascochlorin Derivatives

To confirm the structures of various ascochlorin derivatives, IR measurement was performed. The results obtained are shown below.

Starting AC

| No. | Starting AC | cm$^{-1}$ |
|---|---|---|
| | AC | 3384, 2690, 2926, 2875, 1704, 1629, 1457, 1423, 1374, 1284, ------ |
| | MAC | 3422, 2966, 1715, 1641, 1600, 1449, 1399, 1355, 1286, 1269, 1249, 1229, 1108, 1003, 972, 790 |
| | AS-6 | 3447, 2938, 1738, 1712, 1638, 1456, 1431, 1407, 1364, 1308, 1249, 1228, 1121, 967, 955, 792, 727, 638 |
| | AF | 3367, 2974, 2928, 1739, 1633, 1420, 1283, 1246, 1110, 822, 593 |

AcAC

| No. | AcAC | cm$^{-1}$ |
|---|---|---|
| 22 | diAcAC | 2973, 2874, 1779, 1703, 1450, 1369, 1299, 1256, 1169, 1082 |
| 34 | AcAC | 2973, 1779, 1711, 1642, 1411, 1372, 1294, 1246, 1193, 1093, 1008, 970 |
| 36, 37 | AcAC | 3423, 2970, 1774, 1712, 1642, 1375, 1292, 1248, 1192, 1092 |
| 43 | AcMAC | 2974, 2873, 1774, 1700, 1585, 1369, 1307, 1176, 1095, 970, 755 |
| 45 | diAcAF | 2978, 1755, 1699, 1589, 1560, 1369, 1300, 1187, 1078, 1000, 878, 755 |

AC Schiff Base

| No. | AC Schiff base | cm$^{-1}$ |
|---|---|---|
| 6, 8 | AC + GlyOMe | 3418, 2971, 1739, 1709, 1622, 1437, 1254, 1208, 1180, 1111, 969 |
| 13 | AC + GlyNH$_2$ | 3439, 2974, 1698, 1666, 1606, 1419, 1252, 1109, 969 |
| 16 | AC + NAcLysOH | 3420, 3385, 2931, 1705, 1634, 1252, 1111, 1016, 970, 908, 755 |
| 31 | AC + aAlaNH$_2$ | 3161, 2972, 1677, 1627, 1541, 1445, 1252, 1112, 969, 756 |
| 41 | AC + PheNH$_2$ | 3422, 2956, 1710, 1623, 1543, 1437, 1375, 1254, 1171, 1110, 1013, 970 |

MAC Schiff base

| No. | MAC Schiff base | cm$^{-1}$ |
|---|---|---|
| 10 | MAC + GlyOMe | 3445, 2972, 1749, 1710, 1625, 1417, 1252, 1203, 1108, 1016, 970 |
| 11 | MAC + GlyNH$_2$ | 3423, 2972, 2936, 1702, 1620, 1414, 1251, 1109, 1012, 970 |
| 14 | MAC + NAcLysOH | 3384, 3418, 2934, 1704, 1633, 1421, 1249, 1116, 1020, 730 |
| 25 | MAC + âAlaNH$_2$ | 2971, 1673, 1623, 1416, 1250, 1109, 1012 |
| 40 | MAC + PheNH$_2$ | 3446, 2936, 1711, 1621, 1454, 1414, 1358, 1250, 1167, 1108, 1003, 970, 751, 698 |
| 42 | MAC + AlaNH$_2$ | 3346, 3190, 2974, 2936, 2873, 1702, 1615, 1452, 1414, 1374, 1251, 1109, 970, 756 |

AS-6 Schiff Base

| No. | AS-6 Schiff base | cm$^{-1}$ |
|---|---|---|
| 17 | AS-6 + GlyNH$_2$ | 3419, 2977, 2939, 2677, 2605, 2497, 1702, 1618, 1475, 1398, 1316, 1252, 1114, 1037 |
| 18 | AS-6 + GlyOMe | 3447, 2956, 1748, 1708, 1623, 1419, 1252, 1205, 1112 |
| 19 | AS-6 + NAcLysOH | |
| 30 | AS-6 + âAlaNH$_2$ | 3407, 2974, 1672, 1622, 1418, 1250, 1115, 1018, 750 |

AF Schiff Base

| No. | AF Schiff base | cm$^{-1}$ |
|---|---|---|
| 15 | AF + GlyNH$_2$ | 3445, 3360, 2974, 2921, 1750, 1682, 1646, 1601, 1434, 1373, 1308, 1254, 1165, 1113, 977, 607 |

AcAC Schiff Base

| No. | AcAC Schiff base | cm$^{-1}$ |
|---|---|---|
| 23 | AcAC + GlyNH$_2$ | 3346, 2971, 2873, 1777, 1703, 1626, 1422, 1370, 1291, 1250, 1200, 1095 |
| 26 | AcAC + GlyOMe | 2957, 1753, 1709, 1628, 1424, 1372, 1251, 1200, 1097, 1014 |
| 27 | AcAC + âAlaNH$_2$ | 3425, 2972, 1776, 1674, 1628, 1423, 1371, 1200, 1095 |
| 39 | AcAC + PheNH$_2$ | 3442, 2971, 1777, 1736, 1711, 1626, 1454, 1421, 1371, 1249, 1198, 1096, 1010, 970 |
| 44 | AcAC + AlaNH$_2$ | 3734, 2974, 1777, 1704, 1621, 1421, 1371, 1250, 1200, 1089, 970, 788 |

AcAF Schiff Base

| No. | AcAF Schiff base | cm$^{-1}$ |
|---|---|---|
| 48 | AcAF + AlaNH$_2$ | 3195, 2978, 2929, 1754, 1686, 1621, 1421, 1372, 1249, 1195, 1173, 1113 |

Acetal of AC

| No. | Acetal of AC | cm$^{-1}$ |
|---|---|---|
| 32 | diMeAcAC | 3290, 2972, 1778, 1711, 1415, 1371, 1231, 1200, 1108, 1055, 968 |
| 35 | diEtAcAC | 3264, 2975, 1778, 1712, 1414, 1371, 1327, 1231, 1200, 1101, 1048, 1003 |
| 46 | diEtMAC | 3289, 2977, 2933, 1703, 1608, 1575, 1449, 1408, 1388, 1373, 1326, 1108, 1069, 1053, 979 |
| 47 | diEtAcAF | 2978, 1752, 1638, 1373, 1196, 1050, 998, 752, 664 |
| 49 | diBuMAC | 3303, 2959, 2872, 1712, 1605, 1571, 1454, 1405, 1328, 1227, 1107, 970 |
| 50 | PGMAC | 3315, 2972, 2870, 1710, 1573, 1456, 1396, 1331, 1238, 1110, 987 |

7. NMR Data of Ascochlorin Derivatives

To confirm the structures of various ascochlorin derivatives, IR measurement was performed. The results obtained are shown below.

1) The structure of each acetylascochlorin compound was confirmed by disappearance of the hydrogen of the phenolic hydroxyl group and appearance of hydrogens of an acetoxy group as a result of acetylation.
2) The structure of each Schiff base was confirmed by disappearance of the aldehyde hydrogen, appearance of an azomethine hydrogen, and appearance of hydrogen(s) belonging to the attached amino acid derivative.
3) The structure of an acetal of each AC compound was confirmed by disappearance of the aldehyde hydrogen, detection of a dioxymethine hydrogen, and detection of hydrogen(s) belonging to the attached alcohol.

| No. | Starting AC | 2-OH | Ar—CHO | 4-OH |
|---|---|---|---|---|
| 1 | AC | 12.68 | 10.12 | 6.37 |
| 1 | MAC | 12.51 | 10.23 | |
| 17 | AS-6 | | 10.26 | 10.26 |
| 15 | AF | 12.67 | 10.12 | 6.43 | unit: ppm

| No. | AcAC | 2-OH | Ar—CHO | —OCOCH$_3$ |
|---|---|---|---|---|
| 22 | diAcAC | | 10.25 | 2.33, 2.32 |
| 34, 36 | AcAC | 12.53 | 10.28 | 2.35 |
| 43 | AcMAC | | 10.22 | 2.33 |
| 45 | diAcAF | | 10.24 | 2.34, 2.33 | unit: ppm

| No. | Schiff base-1 | | Ar—CH=N— | —CH$_2$CO— | —CO$_2$CH$_3$ |
|---|---|---|---|---|---|
| 6 | AC | GlyOMe | 8.59 | 4.35 | 3.77 |
| 10 | MAC | GlyOMe | 8.67 | 4.38 | 3.77 |
| 18 | AS-6 | GlyOMe | 8.58 | 4.35 | 3.76 |
| 26 | AcAC | GlyOMe | 8.69 | 4.40 | 3.77, 2.33 | unit: ppm

| No. | Schiff base-2 | | Ar—CH=N— | —CH$_2$CO— | —OCOCH$_3$ |
|---|---|---|---|---|---|
| 11 | MAC | GlyNH$_2$ | 8.71 | 4.33 | |
| 13 | AC | GlyNH$_2$ | 8.63 | 4.30 | |
| 15 | AF | GlyNH$_2$ | 8.62 | 4.29 | |
| 17 | AS-6 | GlyNH$_2$ | 8.69 | 4.32 | |
| 23 | AcAC | GlyNH$_2$ | 8.73 | 4.34 | 2.35 | unit: ppm

| No. | Schiff base-3 | | Ar—CH=N— | —CH(NHAc)CO$_2$H | =N—CH$_2$— | —NHCOCH$_3$ |
|---|---|---|---|---|---|---|
| 14 | MAC | NAcLysOH | 8.47 | 4.30 | 3.46 | 2.35 |
| 16 | AC | NAcLysOH | 8.29 | 4.27 | 3.45 | 2.31 |
| 19 | AS-6 | NAcLysOH | 8.48 | 4.30 | 3.47 | 2.35 | unit: ppm

| No. | Schiff base-4 | | Ar—CH=N— | =NCH$_2$CH$_2$— | —CH$_2$CONH$_2$ | —OCOCH$_3$ |
|---|---|---|---|---|---|---|
| 25 | MAC | âAlaNH$_2$ | 8.69 | 3.89 | 2.60 | |
| 27, 37 | AcAC | âAlaNH$_2$ | 8.71 | 3.91 | 2.61 | 2.33 |
| 30 | AS-6 | âAlaNH$_2$ | 8.67 | 3.89 | 2.62 | |
| 31 | AC | âAlaNH$_2$ | 8.60 | 3.87 | 2.61 | | unit: ppm

| No. | Schiff base-5 | | Ar—CH=N— | PhH | —CH(Bn)CONH$_2$ | —OCOCH$_3$ |
|---|---|---|---|---|---|---|
| 39 | AcAC | PheNH$_2$ | 8.63 | 7.31 | 4.12 | 2.33 |
| 40 | MAC | PheNH$_2$ | 8.63 | 7.31 | 4.10 | |
| 41 | AC | PheNH$_2$ | 8.43 | | 4.09 | | unit: ppm

| No. | Schiff base-6 | | Ar—CH=N— | —CH(Me)CONH$_2$ | —CH(CH$_3$)CONH$_2$ | —OCOCH$_3$ |
|---|---|---|---|---|---|---|
| 42 | MAC | AlaNH$_2$ | 8.72 | 4.04 | 1.58 | |
| 44 | AcAC | AlaNH$_2$ | 8.74 | 4.04 | 1.58 | 2.34 |
| 48 | AcAF | AlaNH$_2$ | 8.74 | 4.04 | 1.59 | 2.34 | unit: ppm

| No. | Acetal-1 of AC | 2-OH | —CH(OMe)₂ | —CH(OCH₃)₂ | —OCOCH₃ |
|---|---|---|---|---|---|
| 32 | diMe AcAC | 9.21 | 5.65 | 3.41 | 2.32 | unit: ppm

| No. | Acetal-2 of AC | 2-OH | —CH(OEt)₂ | —CH(OCH₂CH₃)₂ | —OCOCH₃ | —CH(OCH₂CH₃)₂ |
|---|---|---|---|---|---|---|
| 35 | diEt AcAC | 9.44 | 5.76 | 3.54 | 2.31 | 1.24 |
| 46 | diEt MAC | 9.32 | 5.76 | 3.65 |  | 1.24 |
| 47 | diEt AcAF | 9.40 | 5.76 | 3.64 | 2.31 | 1.24 | unit: ppm

| No. | Acetal-3 of AC | 2-OH | —CH(OBu)₂ | —CH(OCH₂—Pr)₂ | —CH(OC₃H₆—CH₃)₂ |
|---|---|---|---|---|---|
| 49 | diBu MAC | 9.31 | 5.74 | 3.57 | 0.89 | unit: ppm

| No. | Acetal-4 of AC | 2-OH | —CH(—OC₃H₆O—) | —CH(—OCH₂CH₂CH₂O—) |
|---|---|---|---|---|
| 50 | PG MAC | 8.82 | 5.81 | 4.30, 3.98 | unit: ppm

8. List of Structural Formulae of Ascochlorin Derivatives

The structural formulae of the ascochlorin derivatives are shown below, which are determined on the basis of the production described in 1 to 4 above and the data obtained in 5 to 7 above.

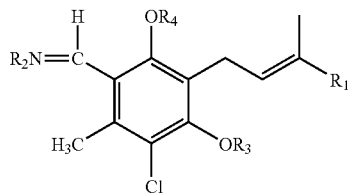

| No. | Abbreviation | R₁ | =N—R₂ | R₃ | R₄ |
|---|---|---|---|---|---|
| 5,7 | AC + LysOH | (structure with NHAc, CO₂H) | (structure with NH₂, CO₂H) | —H | —H |
| 6,8 | AC + GlyOMe | (cyclohexanone with vinyl and methyl substituents) | =N—CH₂CO₂Me | —H | —H |

-continued

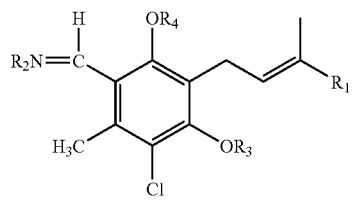

| No. | Abbreviation | R₁ | =N—R₂ | R₃ | R₄ |
|---|---|---|---|---|---|
| 9 | AC + GlyOH | (cyclohexanone with propenyl and methyl substituents) | =N–CH₂–CO₂H | —H | —H |
| 10 | MAC + GlyOMe | (cyclohexanone with propenyl and methyl substituents) | =N–CH₂–CO₂Me | —Me | —H |
| 11 | MAC + GlyNH₂ | (cyclohexanone with propenyl and methyl substituents) | =N–CH₂–CONH₂ | —Me | —H |
| 12 | MAC + GlyOH | (cyclohexanone with propenyl and methyl substituents) | =N–CH₂–CO₂H | —Me | —H |
| 13 | AC + GlyNH₂ | (cyclohexanone with propenyl and methyl substituents) | =N–CH₂–CONH₂ | —H | —H |
| 14 | MAC + NAcLysOH | (cyclohexanone with propenyl and methyl substituents) | =N–(CH₂)₄–CH(NHAc)–CO₂H | —Me | —H |
| 15 | AF + GlyNH₂ | (dihydrofuranone with alkenyl substituent) | =N–CH₂–CONH₂ | —H | —H |

-continued

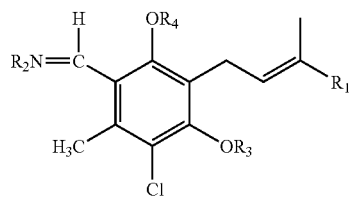

| No. | Abbreviation | R₁ | =N—R₂ | R₃ | R₄ |
|---|---|---|---|---|---|
| 16 | AC + NAcLysOH | (cyclohexanone with propenyl and methyl substituents) | (lysine-NHAc imine) | —H | —H |
| 17 | AS-6 + GlyNH₂ | (cyclohexanone with propenyl and methyl substituents) | =N—CH₂—CONH₂ | —CH₂CO₂H | —H |
| 18 | AS-6 + GlyOMe | (cyclohexanone with propenyl and methyl substituents) | =N—CH₂—CO₂Me | —CH₂CO₂H | —H |
| 19 | AS-6 + NAcLysOH | (cyclohexanone with propenyl and methyl substituents) | (lysine-NHAc imine) | —CH₂CO₂H | —H |
| 20 | MAC + LysOH | (cyclohexanone with propenyl and methyl substituents) | (lysine-NH₂ imine) | —Me | —H |
| 22 | diAcAC | (cyclohexanone with propenyl and methyl substituents) | =O | —Ac | —Ac |

-continued

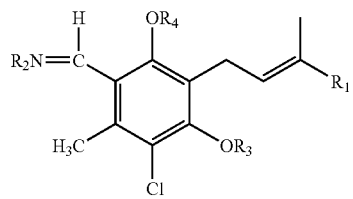

| No. | Abbreviation | R₁ | =N—R₂ | R₃ | R₄ |
|---|---|---|---|---|---|
| 23 | AcAC + GlyNH₂ | (cyclohexanone with propenyl and methyl substituents) | =N−CH₂−CONH₂ | —Ac | —H |
| 25 | MAC + âAlaNH₂ | (cyclohexanone with propenyl and methyl substituents) | =N−CH₂CH₂−CONH₂ | —Me | —H |
| 26 | AcAC + GlyOMe | (cyclohexanone with propenyl and methyl substituents) | =N−CH₂−CO₂Me | —Ac | —H |
| 27 | AcAC + âAlaNH₂ | (cyclohexanone with propenyl and methyl substituents) | =N−CH₂CH₂−CONH₂ | —Ac | —H |
| 28 | MAC + Orn | (cyclohexanone with propenyl and methyl substituents) | =N−(CH₂)₃−CH(NH₂)−CO₂H | —Me | —H |
| 30 | AS-6 + âAlaNH₂ | (cyclohexanone with propenyl and methyl substituents) | =N−CH₂CH₂−CONH₂ | —CH₂CO₂H | —H |

-continued

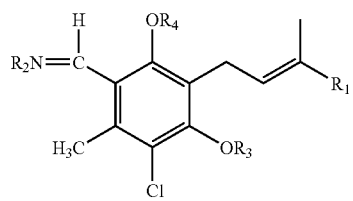

| No. | Abbreviation | R₁ | =N—R₂ | R₃ | R₄ |
|---|---|---|---|---|---|
| 31 | AC + âAlaNH₂ | (cyclohexanone with propenyl and methyl substituents) | =N—CH₂—CH₂—CONH₂ | —H | —H |
| 32 | diMeAcAC | (cyclohexanone with propenyl and methyl substituents) | —OMe, —OMe | —Ac | —H |
| 34 | AcAC | (cyclohexanone with propenyl and methyl substituents) | =O | —Ac | —H |
| 35 | diEtAcAC | (cyclohexanone with propenyl and methyl substituents) | —OEt, —OEt | —Ac | —H |
| 36, 37 | AcAC | (cyclohexanone with propenyl and methyl substituents) | =O | —Ac | —H |
| 37 | AcAC + âAlaNH₂ | (cyclohexanone with propenyl and methyl substituents) | =N—CH₂—CH₂—CONH₂ | —Ac | —H |

-continued

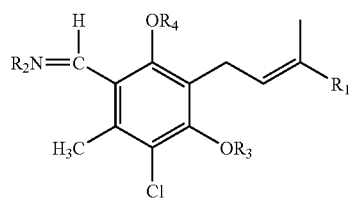

| No. | Abbreviation | R₁ | =N—R₂ | R₃ | R₄ |
|---|---|---|---|---|---|
| 39 | AcAC + PheNH₂ | (cyclohexanone with propenyl and methyl substituents) | =N–CH(CH₂Ph)–CONH₂ | —Ac | —H |
| 40 | MAC + PheNH₂ | (cyclohexanone with propenyl and methyl substituents) | =N–CH(CH₂Ph)–CONH₂ | —Me | —H |
| 41 | AC + PheNH₂ | (cyclohexanone with propenyl and methyl substituents) | =N–CH(CH₂Ph)–CONH₂ | —H | —H |
| 42 | MAC + AlaNH₂ | (cyclohexanone with propenyl and methyl substituents) | =N–CH(CH₃)–CONH₂ | —Me | —H |
| 43 | AcMAC | (cyclohexanone with propenyl and methyl substituents) | =O | —Me | —H |
| 44 | AcAC + AlaNH₂ | (cyclohexanone with propenyl and methyl substituents) | =N–CH(CH₃)–CONH₂ | —Ac | —H |
| 45 | diAcAF | (dihydrofuranone with alkenyl substituent) | =O | —Ac | —Ac |

-continued

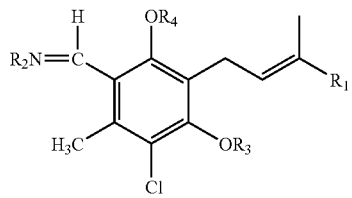

| No. | Abbreviation | R$_1$ | =N—R$_2$ | R$_3$ | R$_4$ |
|---|---|---|---|---|---|
| 46 | diEtMAC | | —OEt, —OEt | —Me | —H |
| 47 | diEtAcAF | | —OEt, —OEt | —Ac | —H |
| 48 | AcAF + AlaNH$_2$ | | (=N–CH(CONH$_2$)–) | —Ac | —H |
| 49 | diBuMAC | | —OBu, —OBu | —Me | —H |
| 50 | PGMAC | | —OCH$_2$CH$_2$CH$_2$O— | —Me | —H |

The method of the present invention is very useful in synthesizing novel ligands which activate nuclear receptors. This is because such ligands have the function of regulating the expression of gene information involved in the onset and exacerbation of lifestyle-related diseases, chronic inflammation and malignant tumors, etc. In particular, ascochlorin and cylindrochlorin are extremely useful as resources for new pharmaceuticals because they can serve as mother compounds for synthesis of novel nuclear receptor ligands when their hydroxyl groups at the 2- and 4-positions are modified with alkyl or acyl groups.

The compound of the present invention may be administered by any route of administration permitted for other drugs available for similar applications and in the form of a pure preparation or an appropriately formulated pharmaceutical composition. Thus, the administration can be accomplished, for example, in the dosage form of solid, semi-solid, lyophilized powder or liquid (e.g., tablets, suppositories, pills, capsules, powders, solutions, suspensions, emulsions, creams, lotions, aerosols, ointments, gels) by oral, intranasal, parenteral or topical route, preferably in an appropriate unit dose form which allows an exact volumetric dosing in one administration. Such a composition is composed of commonly used pharmaceutical carriers or excipients and the compound of the present invention and may also be supplemented with other medical pharmaceuticals and/or various pharmaceutically acceptable additives such as carriers and absorption aids. In general, such a composition acceptable as a formulation may comprise about 1% to 99% by weight of the compound of the present invention and about 99% to 1% by weight of appropriate pharmaceutical additives, depending on the dosage form to be administered. In this composition, the compound of the present invention as a medical pharmaceutical constitutes about 5% to 75% of the composition and the balance comprises appropriate pharmaceutical excipients. The effective daily dose required for the compound of the present invention to ameliorate a pathological condition is 0.1 to 20 mg/kg, desirably 0.2 to 5 mg/kg of body weight for adults.

Dosage forms preferred for the diseases explained in detail above may be achieved by formulating in such a manner as to select a dosage set to be adjustable depending on the severity of the diseases. In formulating, most important is the limitation arising from the fact that the compound of the present invention is fat-soluble. Since ligands for the nuclear receptor superfamily are fat-soluble hormones or vitamins, it is therefore natural to believe that the compound of the present invention is also fat-soluble. Pharmaceutically acceptable additives for use in oral administration may be adjusted by adding any excipient commonly available, including mannite, lactose, starch, magnesium stearate, saccharin sodium, talc, cellulose, glucose, gelatin, sucrose or magnesium carbonate. Such a composition may be in the form of a solution, tablet, pill, capsule, powder or sustained-release formulation, etc.

The composition is preferably in the form of a tablet or a pill, which comprises the compound of the present invention together with a diluent (e.g., lactose, sucrose, dicalcium phosphate), a disintegrating agent (e.g., starch and derivatives thereof), a lubricant (e.g., magnesium stearate), and a binder (e.g., starch, gum arabic, polyvinylpyrrolidone, gelatin, cellulose and derivatives thereof), as well as a surfactant having the ability to water the particle surface of the compound of the present invention which is highly fat-soluble and water-repellent, a fat-soluble additive, bile acid, a phospholipid, etc. It is particularly preferable to comprise an aliphatic synthetic surfactant or an organic solvent-soluble polymeric aid. Examples of these materials include gum arabic, sodium alginate, methylcellulose, carboxymethyl cellulose, hydroxypropylcellulose, polyvinylpyrrolidone, bentonite, sodium lauryl sulfate, Polysorbate 80, sorbitan monofatty acid ester, and polyoxyl 40 stearate.

EXAMPLES

The present invention will now be further illustrated by way of the following examples, which are not intended to limit the scope of the invention.

Example 1

Synthesis of Imino Compounds Starting with Ascochlorin Derivatives

Ascochlorin and its derivatives (Compounds-1 & -2, ascofuranone) were condensed with amino acid derivatives having a primary amine in the presence or absence of a base (e.g., triethylamine, potassium carbonate) and in a solvent (e.g., methanol, tetrahydrofuran (THF)).

After confirming the progress of the reaction (i.e., the formation of imino compounds appearing as band yellow spots) by thin-layer chromatography (TLC), the Schiff bases were extracted from the reaction solutions and then evaporated to remove the solvent under reduced pressure, or alternatively, the reaction solvent was directly distilled off under reduced pressure. In this way, concentrates containing imino compounds were obtained.

The concentrates were purified by silica gel column chromatography to isolate the imino compounds.

Other things to be noted are as shown below.

(1) The yield was varied over a wide range from 10% up to a quantitative level depending on the reactivity.

(2) Each product was an imino compound formed by reaction with the aldehyde group of each starting compound.

(3) Compound-1 and Compound-2 having a protected hydroxyl group at the 4-position are highly reactive.

(4) Glycine amide formed an imino compound with each of the ascochlorin and derivatives thereof.

The results obtained are shown in Tables 4 to 8 below.

TABLE 4

List of compounds along with their yields

Amino compound

| Starting material | Glycine | Glycine methyl ester | Glycine amide | N-Acetyl lysine | Lysine |
|---|---|---|---|---|---|
| AC | 9 (trace) | 6&7 (55%) | 13 (80%) | 16 (10%) | 5&7 (<10%) |
| Compound-1 | 12 (trace) | 10 (81%) | 11 (81%) | 14 (80%) | 20 (<10%) |
| Compound-2 | | | 17 (94%) | 19 (10%) | |
| AF | | | 15 (23%) | | |

Numbers in parentheses: Yields calculated from starting materials
Abbreviations:
GlyOH = glycine,
GlyOMe = glycine methyl ester,
GlyNH$_2$ = glycine amide,
NacLysOH = α-N-acetyl lysine,
LysOH = lysine
AC = ascochlorin,
Compound-1 = 4-O-methylascochlorin,
Compound-2 = 4-O-carboxymethylascochlorin,
AF = ascofuranone

TABLE 5

Thin-layer chromatography: Confirmation of Rf value and purity

| No. | Imino compound | Developing solvent | Rf value | TLC purity |
|---|---|---|---|---|
| 6, 8 | AC GlyOMe | 50% AcOEt/Hexane | 0.33 | One spot |
| 10 | MAC GlyOMe | 50% AcOEt/Hexane | 0.36 | One spot |
| 11 | MAC GlyNH$_2$ | 5% MeOH/CHCl$_3$ | 0.53 | Slightly impure |
| 13 | AC GlyNH$_2$ | 5% MeOH/CHCl$_3$ | 0.57 | One spot |
| 14 | MAC NAcLysOH | 20% MeOH/CHCl$_3$ | 0.04 | Decomposed |
| 15 | AF GlyNH$_2$ | 10% MeOH/CHCl$_3$ | 0.54 | One spot |
| 16 | AC NAcLysOH | 20% MeOH/CHCl$_3$ | 0.27 | One spot |
| 17 | AS-6 GlyNH$_2$ | 20% MeOH/CHCl$_3$ | 0.41 | One spot (containing Et$_3$N) |
| 18 | AS-6 GlyOMe | 20% MeOH/CHCl$_3$ | 0.57 | One spot |

Note)
Et$_3$N: triethylamine
Abbreviations:
GlyOH = glycine,
GlyOMe = glycine methyl ester,
GlyNH$_2$ = glycine amide,
NacLysOH = α-N-acetyl lysine,
LysOH = lysine
AC = ascochlorin,
Compound-1 = 4-O-methylascochlorin,
Compound-2 = 4-O-carboxymethylascochlorin,
AF = ascofuranone

TABLE 6

Infrared absorption (cm$^{-1}$) for carbonyl region

| No. | AC compound | | Carbonyl region cm$^{-1}$ (?: visual judgment) | | | |
|---|---|---|---|---|---|---|
| | AC | | | | 1704 | 1629 |
| | Compound-1 | | | 1715 | | 1641 |
| | Compound-2 | | 1738 | 1712 | | 1638 |
| | AF | | 1739 | | | 1633 |

| No. | Imino compound | | Ketone region cm$^{-1}$ (?: visual judgment) | | | | | |
|---|---|---|---|---|---|---|---|---|
| | AC | | | | 1704 | | 1629 | |
| 6, 8 | AC | GlyOMe | 1739 | 1709 | | | 1621 | ?1602 |
| 13 | AC | GlyNH$_2$ | | | 1698 | 1666 | | 1602 |
| 16 | AC | NAcLysOH | | | 1704 | | 1634 | ?1601 |
| | Compound-1 | | | 1715 | | | 1641 | |
| 10 | " | GlyOMe | 1749 | 1710 | | | 1625 | ?1598 |
| 11 | " | GlyNH$_2$ | | | 1702 | | 1620 | |
| 14 | " | NAcLysOH | | | 1704 | | 1633 | |
| | Compound-2 | | 1738 | 1712 | | | 1638 | |
| 17 | " | GlyNH$_2$ | | | 1702 | | 1618 | |
| 18 | " | GlyOMe | 1748 | 1708 | | | 1622 | ?1600 |
| | AF | | 1739 | | | | 1633 | |
| 15 | AF | GlyNH$_2$ | 1750 | | | 1682 | 1645 | 1600 |

Abbreviations:
GlyOH = glycine,
GlyOMe = glycine methyl ester,
GlyNH$_2$ = glycine amide,
NacLysOH = α-N-acetyl lysine,
LysOH = lysine
AC = ascochlorin,
Compound-1 = 4-O-methylascochlorin,
Compound-2 = 4-O-carboxymethylascochlorin,
AF = ascofuranone

TABLE 7

Nuclear magnetic resonance spectrum-1 (NMR)

| No. | AC compound & imino compound | | Chemical shift (excerpt) ppm |
|---|---|---|---|
| | AC | | 10.1(Ar—CHO) |
| 6, 8 | AC | GlyOMe | 8.6(—N=CH—Ar), 4.3(—CH$_2$CO—), 3.8(—CO$_2$Me) |
| 13 | AC | GlyNH$_2$ | 8.6(—N=CH—Ar), 4.3(—CH$_2$CO—) |
| 16 | AC | NAcLysOH | Structure not yet determined by NMR |
| | Compound-1 | | 10.2(Ar—CHO) |
| 10 | MAC | GlyOMe | 8.6(—N=CH—Ar), 4.3(—CH$_2$CO—), 3.8(—CO$_2$Me) |
| 11 | MAC | GlyNH$_2$ | 8.7(—N=CH—Ar), 4.3(—CH$_2$CO—) |
| 14 | MAC | NAcLysOH | Structure not yet determined by NMR |
| | Compound-2 | | 10.3(Ar—CHO) |
| 17 | AS-6 | GlyNH$_2$ | 8.7(—N=CH—Ar), 4.3(—CH$_2$CO—) |
| 18 | AS-6 | GlyOMe | 8.6(—N=CH—Ar), 4.3(—CH$_2$CO—), 3.8(—CO$_2$Me) |
| | AF | | 10.1(Ar—CHO) |
| 15 | AF | GlyNH$_2$ | 8.6(—N=CH—Ar), 4.3(—CH$_2$CO—) |

Abbreviations:
GlyOH = glycine,
GlyOMe = glycine methyl ester,
GlyNH$_2$ = glycine amide,
NacLysOH = α-N-acetyl lysine,
LysOH = lysine
AC = ascochlorin,
Compound-1 = 4-O-methylascochlorin,
Compound-2 = 4-O-carboxymethylascochlorin,
AF = ascofuranone

TABLE 8

Nuclear magnetic resonance spectrum-2 (NMR)

| No. | AC compound & imino compound | | Chemical shift (excerpt) ppm |
|---|---|---|---|
| | AC | | 10.1(Ar—CHO) |
| 6, 8 | AC | GlyOMe | 8.6(—N=CH—Ar), 4.3(—CH$_2$CO—), 3.8(—CO$_2$Me) |
| 13 | AC | GlyNH$_2$ | 8.6(—N=CH—Ar), 4.3(—CH$_2$CO—) |
| 16 | AC | NAcLysOH | Structure not determined by NMR |
| | Compound-1 | | 10.2(Ar—CHO) |
| 10 | " | GlyOMe | 8.6(—N=CH—Ar), 4.3(—CH$_2$CO—), 3.8(—CO$_2$Me) |
| 11 | " | GlyNH$_2$ | 8.7(—N=CH—Ar), 4.3(—CH$_2$CO—) |
| 14 | " | | Structure not determined by NMR |
| | Compound-2 | | 10.3(Ar—CHO) |
| 17 | " | GlyNH$_2$ | 8.7(—N=CH—Ar), 4.3(—CH$_2$CO—) |
| 18 | " | GlyOMe | 8.6(—N=CH—Ar), 4.3(—CH$_2$CO—), 3.8(—CO$_2$Me) |
| | AF | | 10.1(Ar—CHO) |
| 15 | AF | GlyNH$_2$ | 8.6(—N=CH—Ar), 4.3(—CH$_2$CO—) |

The structures of the synthesized compounds are shown below. Abbreviations in figure: MAC=Compound-1, AS-6=Compound-2

AC, MAC, AS-6, AF
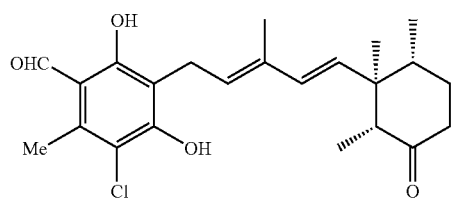
AC: ascochlorin
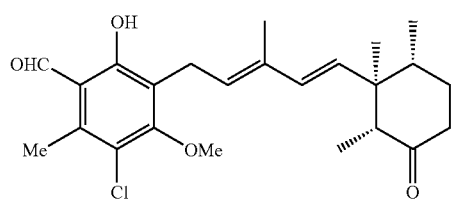
MAC: 4-Omethylascochlorin
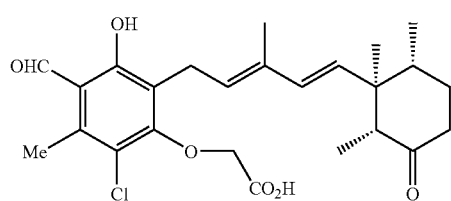
AS-6: 4-O-carboxymethylascochlorin
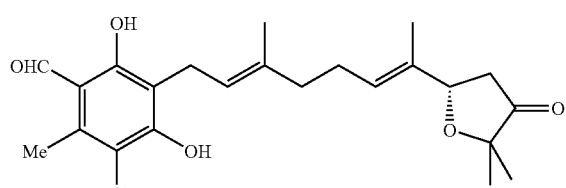
AF: ascofuranone
1) AC deriv's
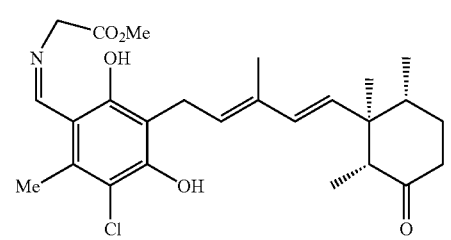
AC + GlyOMe(6,8)
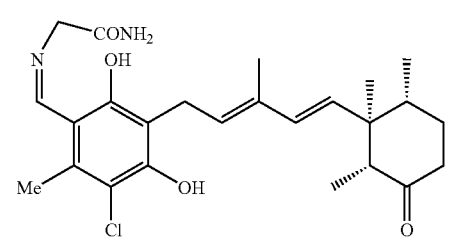
AC + GlyNH$_2$(13)
-continued
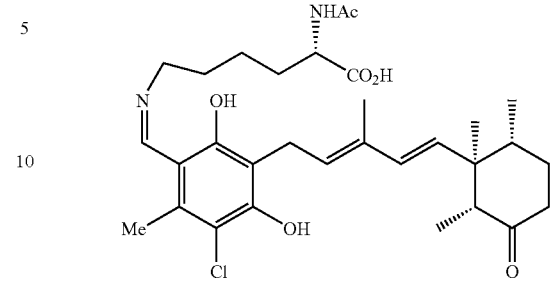
AC + NacLysOH(16)
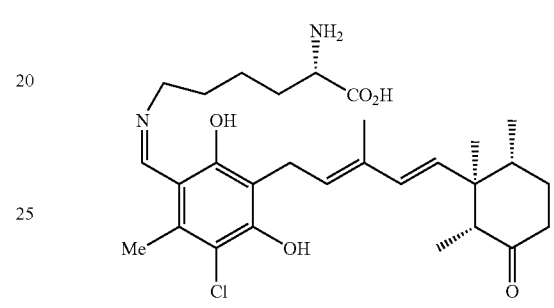
AC + LysOH(5,7)
2) MAC derive's
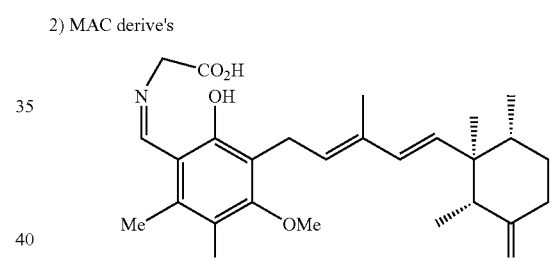
MAC + GlyOH(12)
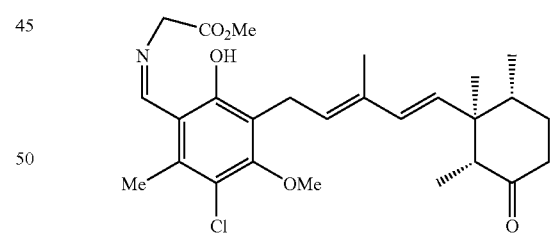
MAC + GlyOMe(10)
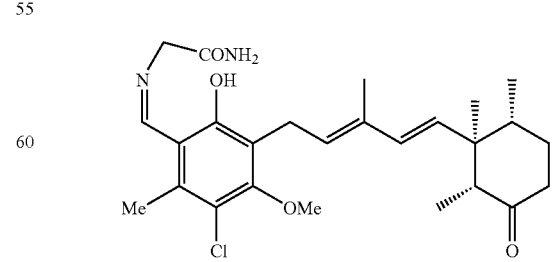
MAC + GlyNH$_2$(11)

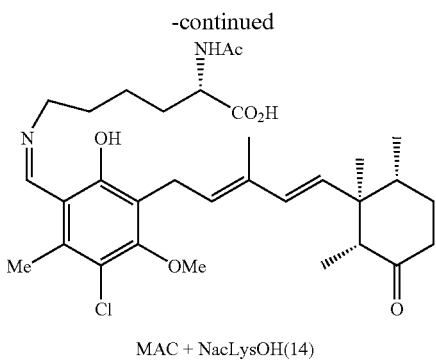

MAC + NacLysOH(14)

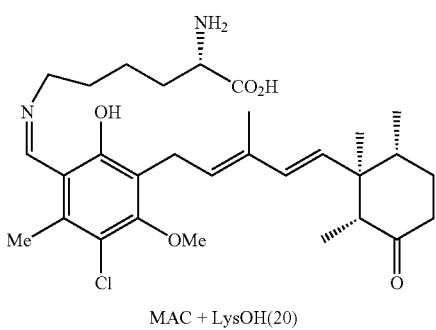

MAC + LysOH(20)

3) AS-6 deriv's

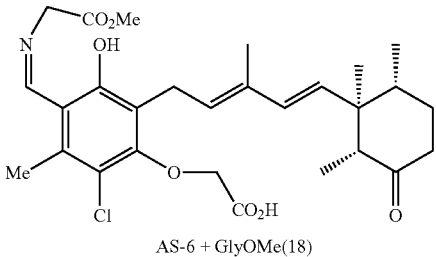

AS-6 + GlyOMe(18)

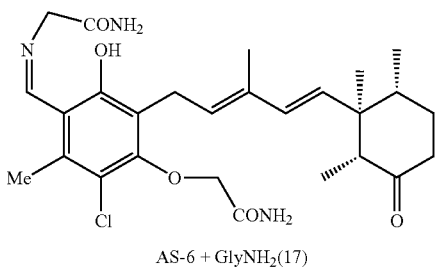

AS-6 + GlyNH₂(17)

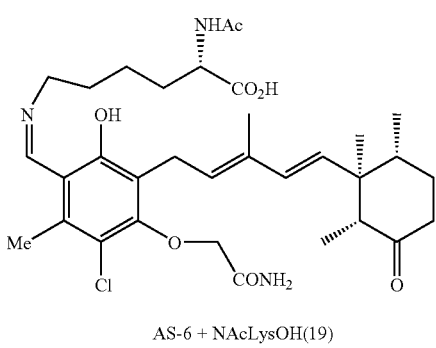

AS-6 + NAcLysOH(19)

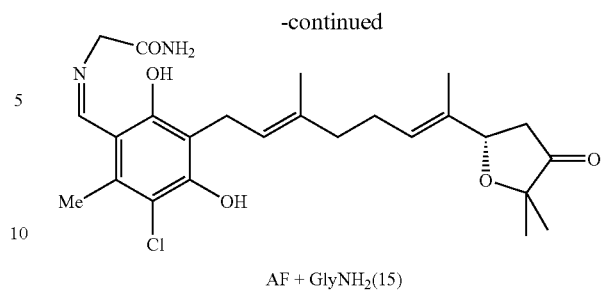

AF + GlyNH₂(15)

(C═N double bond is in the Z configuration in this figure for convenience)

Example 2

Ascochlorin (405 mg, 1 mM) was dissolved in 10 ml tetrahydrofuran and a solution of glycine amide (85 mg, 1.15 mM) in 5% triethylamine-containing methanol (5 ml) was slowly added thereto while stirring at room temperature. After completion of the addition, stirring was continued at room temperature and the reaction was monitored by silica gel thin-layer chromatography. The developing solvent used was methanol:chloroform=5:95. After 16 hours, the spot corresponding to ascochlorin was found to disappear and there was only a yellow spot indicative of a Schiff base between ascochlorin and glycine amide (Rf: 0.57); the reaction solution was concentrated to dryness under reduced pressure. The dried yellow amorphous powder was dissolved in a small amount of methanol and separated by silica gel column chromatography (solvent: 10% methanol-containing dichloromethane) into the Schiff base and impurities. The yellow eluates containing only the Schiff base were collected and evaporated to dryness under reduced pressure to give the Schiff base formed between the aldehyde group of ascochlorin and an amino group of glycine amide (367 mg, yield 80%).

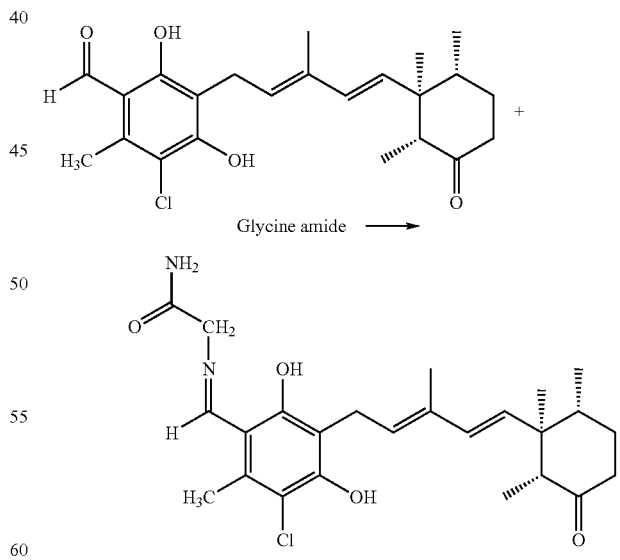

Infrared absorption band (cm$^{-1}$): 3420, 2974, 1698, 1666, 1606, 1419, 1252, 1112, 969

Nuclear magnetic resonance spectrum: The structure was determined by disappearance of the aldehyde proton of ascochlorin, appearance of an azomethine proton, and appearance of protons belonging to the methylene group of glycine amide. The chemical shifts of protons attached to these groups are as follows: Ar—CH=N—; 8.63, —CH₂CONH₂; 4.38 (unit: ppm), where Ar in Ar—CH=N— represents a molecule formed by removing aldehyde from ascochlorin, and —C= in —C=N— represents the aldehyde carbon of ascochlorin attached to an amino group of glycine amide.

Elemental Analysis (Calculated for C₂₅H₃₃O₄N₂Cl): C, 65.15; H, 7.17; N, 6.08, Cl 7.71. (Found): C, 65.08; H, 7.20; N, 6.05, Cl 7.82.

Example 3

Diacetylascochlorin (490 mg, about 1 mM) and β-alanine amide (176 mg, 2 mM) were dissolved in 50 ml tetrahydrofuran and boiled under reflux for 1 hour. After 1 hour, when examining by silica gel thin-layer chromatography (developing solvent: 10% methanol-containing chloroform), the spot corresponding to acetylascochlorin was found to disappear and there was only a yellow spot indicative of a Schiff base between acetylascochlorin and β-alanine amide; the reaction solution was rapidly cooled to room temperature and concentrated to dryness under reduced pressure. The product obtained was a yellow amorphous powder. This yellow powder was dissolved in a small amount of methanol and applied to silica gel column chromatography as in the case of Example 1 to give the Schiff base (molecular formula: C₂₈H₃₇O₄N₂Cl, molecular weight: 516.5) formed between the aldehyde group of acetylascochlorin and an amino group of β-alanine amide as a yellow amorphous powder (507 mg, yield 98%).

Infrared absorption band (cm⁻¹): 3425, 2972, 1776, 1674, 1628, 1423, 1371, 1200, 1095

Nuclear magnetic resonance spectrum: The structure was determined by disappearance of the aldehyde proton of ascochlorin, appearance of an azomethine proton, and appearance of protons belonging to the methylene groups of glycine amide. The chemical shifts of protons attached to these groups are as follows: Ar—CH=N—; 8.71, =N—C H₂—CH₂CONH₂; 3.91, =N—CH₂—CH₂CONH₂; 2.61, —O—COCH₃; 2.33 (unit: ppm), where Ar in Ar—CH=N— represents a molecule formed by removing aldehyde from ascochlorin, and —C= in —C=N— represents the aldehyde carbon of ascochlorin attached to an amino group of β-alanine amide.

Elemental Analysis (Calculated for C₂₈H₃₇O₅N₂Cl): C, 65.05; H, 7.16; N, 6.08, Cl 5.42. (Found): C, 64.98; H, 7.22; N, 6.05, Cl 5.72.

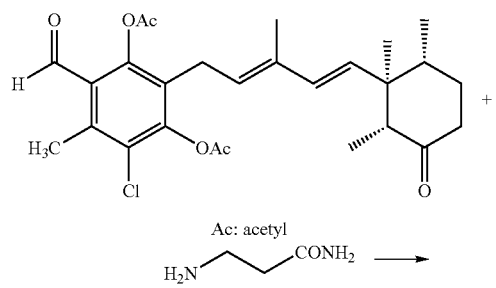

-continued

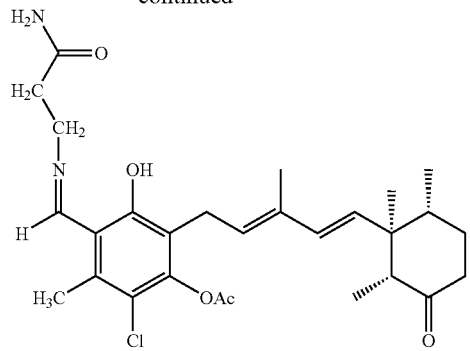

Example 4

4-O-Methylascochlorin (420 mg, about 1 mM) and L-phenylalanine amide (200 mg, 1.22 mM) were dissolved by heating in 20 ml tetrahydrofuran. After dissolution, 30 mg of triethylamine was added to start the reaction while stirring at room temperature. The reaction was monitored by silica gel thin-layer chromatography using a 1:9 mixture of methanol and chloroform as a developing solvent. After 16 hours, the spot corresponding to 4-O-methylascochlorin was found to disappear and there was only a yellow spot indicative of a Schiff base (Rf: 0.36); the reaction solution was concentrated to dryness under reduced pressure. The resulting yellow amorphous powder was dissolved in a small amount of methanol and applied to silica gel column chromatography (solvent: 10% methanol-containing dichloromethane) to purify the Schiff base. The yellow eluates containing only the Schiff base were collected and evaporated to dryness under reduced pressure to give the Schiff base formed between the aldehyde group of 4-O-methylascochlorin and an amino group of L-phenylalanine amide (423 mg, yield 75%).

Infrared absorption band (cm⁻¹): 3446, 2936, 1711, 1621, 1454, 1414, 1358, 1250, 1167, 1108, 1008, 970, 751, 698

Nuclear magnetic resonance spectrum: The structure was determined by disappearance of the aldehyde proton of ascochlorin, appearance of an azomethine proton, and appearance of protons belonging to the methine group and the phenylalanine aromatic ring of phenylalanine amide. The chemical shifts of protons attached to these groups are as follows: Ar—CH=N—; 8.63, PhH; 7.31, —CHCONH₂; 4.10 (unit: ppm), where Ar in Ar—CH=N— represents a molecule formed by removing aldehyde from ascochlorin, and —C= in —C=N— represents the aldehyde carbon of ascochlorin attached to an amino group of glycine amide.

Elemental Analysis (Calculated for C₃₃H₄₁O₄N₂Cl): C, 70.15; H, 7.26; N, 4.96, Cl 6.29. (Found): C, 70.28; H, 7.19; N, 5.05, Cl 6.33.

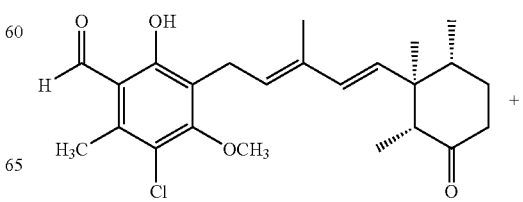

-continued

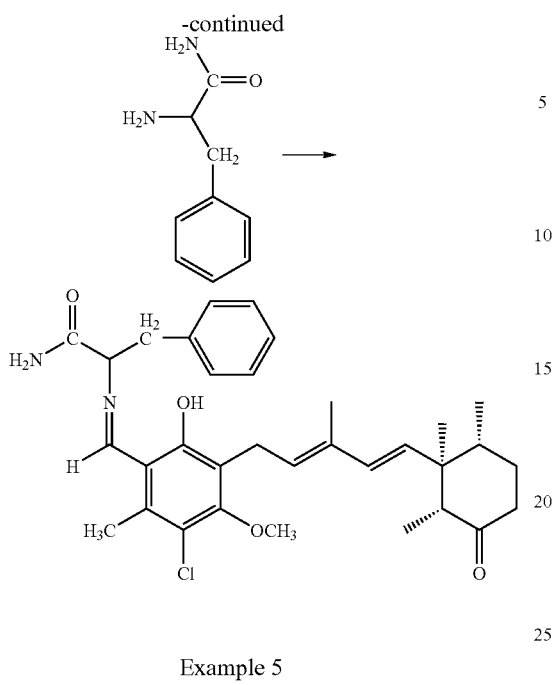

Example 5

4-O-Carboxymethylascochlorin (463 mg, about 1 mM) and α-N-acetyl-L-lysine (300 mg, about 1.6 mM) were dissolved by heating in 50 ml methanol and reacted while stirring at room temperature in the presence of finely powdered potassium carbonate (50 mg) as a catalyst. When the reaction was monitored by silica gel thin-layer chromatography, after 16 hours, the spot corresponding to the starting material 4-O-carboxymethylascochlorin was found to disappear and there was only a yellow spot of the reaction product. The reaction solution was immediately concentrated under reduced pressure to remove the solvent and the residue was evaporated to dryness in a vacuum desiccator. The resulting yellow amorphous powder was then dissolved in a small amount of methanol and applied to silica gel column chromatography (solvent: 20% methanol-containing dichloromethane) to purify the formed Schiff base. The yellow eluates containing only the Schiff base were collected and evaporated to dryness under reduced pressure to give the Schiff base formed between the aldehyde group of 4-O-carboxymethylascochlorin and the free amino group of α-N-acetyl-L-lysine (278 mg, yield 44%).

Nuclear magnetic resonance spectrum: The structure was determined by disappearance of the aldehyde proton of ascochlorin, appearance of an azomethine proton, and appearance of protons from α-N-acetyl-L-lysine (i.e., protons from methane, methylene adjacent to the nitrogen, and methyl of the α-N-acetyl group). The chemical shifts of protons attached to these groups are as follows: Ar—C$\underline{H}$=N—; 8.48, —C$\underline{H}$(NHCOCH$_3$)COOH; 4.30, =N—CH$_2$—; 3.47, —NH-COCH$_3$; 2.35 (unit: ppm).

Elemental Analysis (Calculated for $C_{33}H_{45}O_8N_2Cl$): C, 62.61; H, 7.11; N, 4.43, Cl 5.61. (Found): C, 62.88; H, 7.14; N, 4.37, Cl 5.80.

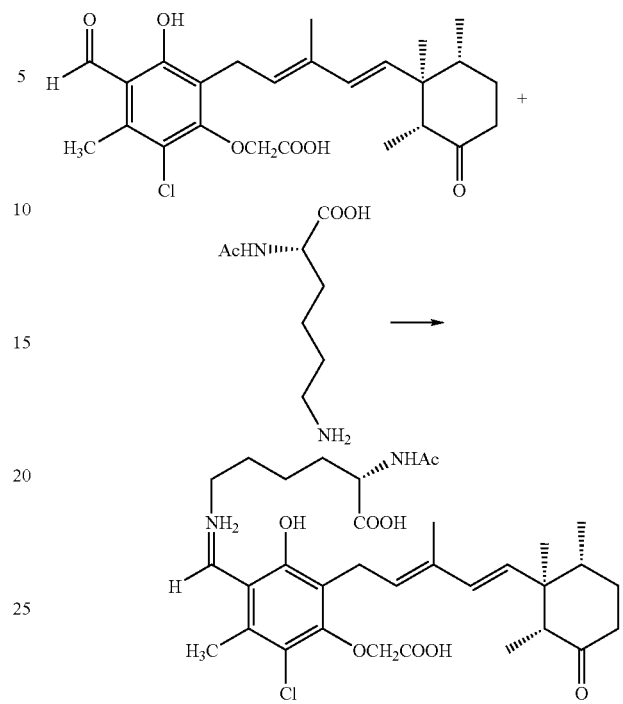

Example 6

Effect on Genetically Obese Diabetic Mice C57BL/ksj db/db(db/db Mice)

A solution of Compound-16 (1 g) in acetone (about 50 ml) was sprinkled over and mixed well with 1 kg of rodent standard feed (CE-2, CLEA Japan, Inc., Japan), followed by air-drying in a chamber. The content of Compound-16 in this feed was about 0.1%. In the same manner, pellet chow samples containing 0.05% to 0.025% of Compound-16 were prepared and used for the experiment. To prepare control feed, the same powder feed was sprinkled with acetone and palletized. Twenty male db/db mice (8 weeks of age after birth) were randomly divided into 4 groups. Each group was housed in a cage for urine collection and fed with the Compound-16-containing feed or the control feed for 21 days. During the housing, the mice were allowed to take feed and water ad libitum and their urine was collected at the intervals indicated in Table 1 to determine urinary sugar excretion by an enzymatic method. The level of urinary sugar excretion was expressed as the mean per animal.

TABLE 9

Effect of Compound-16 to reduce urinary sugar excretion

| (%) | Level of urinary sugar excretion (mg/mouse/day) | | | | | |
|---|---|---|---|---|---|---|
| | 0 days[1] | 1 day | 3 days | 7 days | 14 days | 21 days |
| 0.1 | 814 | 187 | 30 | 15 | 10 | 10 |
| 0.05 | 786 | 541 | 231 | 253 | 170 | 52 |
| 0.025 | 890 | 600 | 452 | 175 | 201 | 134 |
| Control group | 721 | 802 | 760 | 777 | 860 | 858 |

[1] Urine was collected for 24 hours beginning 1 day before initiation of the experiment.

Example 7

Effect of Lowering Serum Cholesterol in Normal Mice

Fifty ICR male mice (5 weeks of age) were randomly divided into 5 groups of 10 animals each and housed in polycarbonate cages at 5 animals per cage. One group for use as a control group was fed with standard feed powder for mice alone, while the other 4 groups were fed for 1 week with the same feed powder supplemented with 0.05% of 4 powdered ascochlorin carboxylic acid derivatives, respectively. With respect to body weight gain during the experiment, each group showed no statistically significant difference over the control group, and there was no effect induced by drug administration. After 1 week, the blood was collected from the heart of each mouse to determine the level of serum total cholesterol by an enzymatic method.

TABLE 10

Effect of ascochlorin derivatives to lower serum cholesterol

| Compound name (added at 0.1%) | Serum total cholesterol (mg/dl) | Remarks |
| --- | --- | --- |
| Control group | 143 | |
| Compound-8 | 93*** | Not toxic |
| Compound-13 | 112** | " |
| Compound-10 | 125* | " |
| Compound-19 | 95** | " |

Student's t-test:
*P < 0.05,
**P < 0.01 and
***P < 0.001

Figure 2:
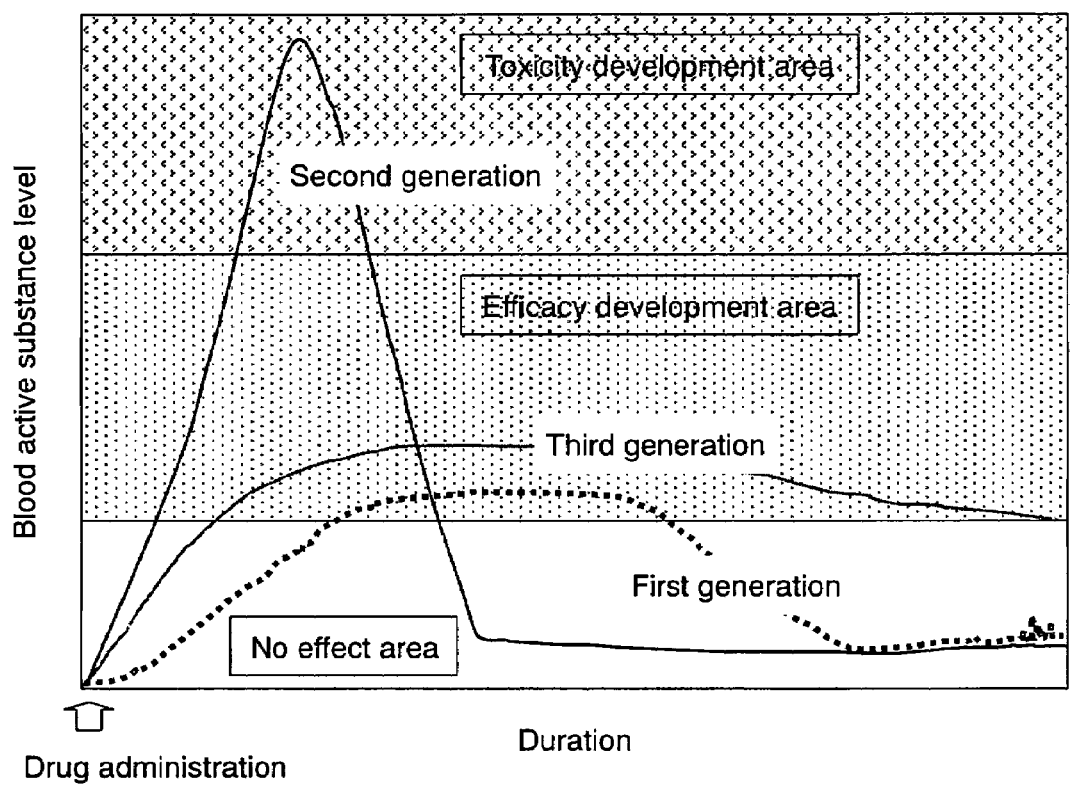
FIG. 2 is a graph illustrating the relationship between duration and blood active substance level for each case of first-, second- and third-generation drugs.

As shown in FIGS. 1 and 2, prenylphenol is attached to the ω-amino group of a feed protein lysine residue through aminocarbonyl reaction to form a Schiff base. When taken by animals, the Schiff base will be hydrolyzed in the small intestine by the action of protease to generate an imino compound in which prenylphenol is attached to the ω-amino group of lysine. Since this imino compound is easily dissolved in water, it will be readily absorbed from the small intestine and cause an exchange reaction with serum albumin in the blood, so that prenylphenol is transferred to a lysine residue ω-amino group of serum albumin. Serum albumin having prenylphenol attached to its ω-amino group will be taken up by target organ cells, where the albumin will be degraded to regenerate prenylphenol. Namely, prenylphenol covalently attached to feed protein will be absorbed, delivered through the blood and reach target cells with its toxicity being masked, thereby exerting its efficacy without showing strong toxicity.

INDUSTRIAL APPLICABILITY

The imino compound (Schiff base) of the present invention is useful in treating and/or preventing diabetes, in treating arteriosclerosis, in lowering serum cholesterol, in treating multiple risk factor syndrome, in treating hypertension, in treating myxedema, in treating chronic inflammation, and in preventing and/or treating restenosis of arterial lumen dilated with a balloon catheter or stent, etc. Moreover, it is also useful as a survival promoter for ensuring survival of cells or tissues differentiated and induced from stem cells to be transplanted to a recipient in regenerative medicine. Further, the imino compound of the present invention is a compound belonging to the third generation shown in FIG. 2 and hence shows a significant effect on the duration of efficacy.

In view of the foregoing, the compound of the present invention is extremely promising as a pharmaceutical preparation because it is effective for various diseases and has a longer duration.

The invention claimed is:

1. A compound of the following formula or a pharmaceutically acceptable salt of the compound or optical isomers thereof:

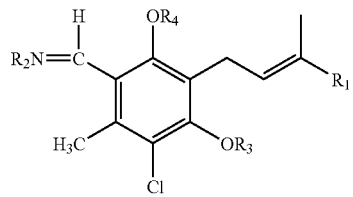

(wherein
R$_1$ represents one of the following two groups:

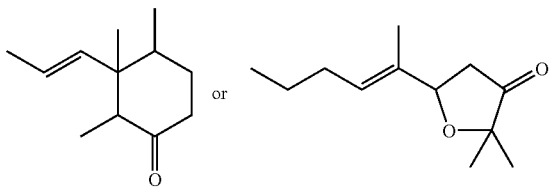

R$_2$ represents —(CH$_2$)$_n$—CHR$_5$R$_6$ (wherein R$_5$ represents a hydrogen atom, an amino group, an amino group substituted with one or two C$_{1-6}$ alkyl groups, or a C$_{1-6}$ alkyl group substituted with phenyl, R$_6$ represents a carboxyl group, —CONH$_2$, or —COOR$_7$ (wherein R$_7$ represents a substituted or unsubstituted C$_{1-6}$ alkyl group), and n represents 0 or an integer of 1 to 6) or a residue formed by removing NH$_2$ from any amino acid, R$_3$ represents a hydrogen atom, a substituted or unsubstituted C$_{1-6}$ alkyl group, a substituted or unsubstituted C$_{2-6}$ alkenyl group, a substituted or unsubstituted C$_{2-6}$ alkynyl group, a substituted or unsubstituted C$_{3-8}$ cycloalkyl group, an acyl group, an aryl group or a carboxyl group, and R$_4$ represents a hydrogen atom, a substituted or unsubstituted C$_{1-6}$ alkyl group, a substituted or unsubstituted C$_{2-6}$ alkenyl group, a substituted or unsubstituted C$_{2-6}$ alkynyl group, a substituted or unsubstituted C$_{3-8}$ cycloalkyl group, an acyl group, an aryl group or a carboxyl group).

2. The compound according to claim 1, wherein R$_4$ is a substituted or unsubstituted C$_{1-6}$ alkyl group, or a pharmaceutically acceptable salt of the compound or optical isomers thereof.

3. The compound according to claim 1, wherein R$_4$ is an acyl group, or a pharmaceutically acceptable salt of the compound or optical isomers thereof.

4. The compound according to claim 1, wherein R$_3$ is a substituted or unsubstituted C$_{1-6}$ alkyl group, or a pharmaceutically acceptable salt of the compound or optical isomers thereof.

5. The compound according to claim 1, wherein R$_3$ and R$_4$, which may be the same or different, are each a substituted or unsubstituted C$_{1-6}$ alkyl group, or a pharmaceutically acceptable salt of the compound or optical isomers thereof.

6. The compound according to claim 1, wherein $R_3$ is a substituted or unsubstituted $C_{1-6}$ alkyl group and $R_4$ is an acyl group, or a pharmaceutically acceptable salt of the compound or optical isomers thereof.

7. The compound according to claim 1, wherein $R_3$ is an acyl group and $R_4$ is a substituted or unsubstituted $C_{1-6}$ alkyl group, or a pharmaceutically acceptable salt of the compound or optical isomers thereof.

8. A pharmaceutical composition which comprises one or more members of a compound of the following formula or a pharmaceutically acceptable salt of the compound or optical isomers thereof, as well as a pharmaceutically acceptable additive including a carrier and a diluent:

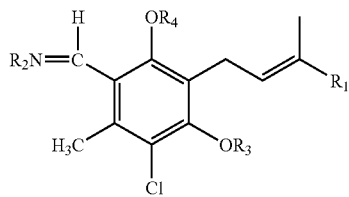

(wherein $R_1$ represents one of the following two groups:

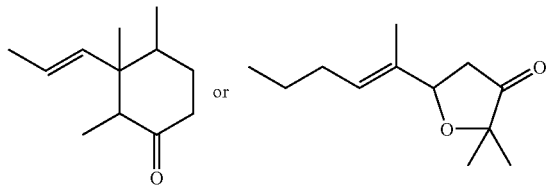

$R_2$ represents —$(CH_2)_n$—$CHR_5R_6$ (wherein $R_5$ represents a hydrogen atom, an amino group, an amino group substituted with one or two $C_{1-6}$ alkyl groups, or a $C_{1-6}$ alkyl group substituted with phenyl, $R_6$ represents a carboxyl group, —$CONH_2$, or —$COOR_7$ (wherein $R_7$ represents a substituted or unsubstituted $C_{1-6}$ alkyl group), and n represents 0 or an integer of 1 to 6) or a residue formed by removing $NH_2$ from any amino acid, $R_3$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group, and $R_4$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, an acyl group, an aryl group or a carboxyl group).

9. A method for treating diabetes, which comprises administering to a patient a therapeutically effective amount of one or more members of the compound according to claim 1 or a pharmaceutically acceptable salt of the compound or optical isomers thereof.

10. A method for treating arteriosclerosis, which comprises administering to a patient a therapeutically effective amount of one or more members of the compound according to claim 1 or a pharmaceutically acceptable salt of the compound or optical isomers thereof.

11. A method for lowering serum cholesterol, which comprises administering to a patient a therapeutically effective amount of one or more members of the compound according to claim 1 or a pharmaceutically acceptable salt of the compound or optical isomers thereof.

12. The compound according to claim 1, wherein $R_2$ is a residue formed by removing $NH_2$ from glycine, N-acetyllysine or β-alanine, $R_3$ is a hydrogen atom, a methyl group or a carboxymethyl group, and $R_4$ is a hydrogen atom, or a pharmaceutically acceptable salt of the compound or optical isomers thereof.

13. A Schiff base of claim 1 which is 3-[5-[1(R),2(S),6(S)-trimethyl-3-oxocyclohexyl]-3-methyl-2,4-pentadienyl]-2-hydroxyl-4-methoxy-5-chloro-6-methylbenzaldehyde and glycinamide (Compound No. 11).

14. A Schiff base of claim 1, which is 3-[5-[1(R),2(S),6(S)-trimethyl-3-oxocyclohexyl]-3-methyl-2,4-pentadienyl]-2-hydroxyl-4-methoxy-5-chloro-6-methylbenzaldehyde and N-acetyllysine (Compound No. 14).

15. A Schiff base of claim 1, which is 3-[5-[1(R),2(S),6(S)-trimethyl-3-oxocyclohexyl]-3-methyl-2,4-pentadienyl]-2-hydroxyl-4-carboxymethoxy-5-chloro-6-methylbenzaldehyde and N-acetyllysine (Compound No. 19).

16. A Schiff base of claim 1, which is 3-[5-[1(R),2(S),6(S)-trimethyl-3-oxocyclohexyl]-3-methyl-2,4-pentadienyl]-2-hydroxyl-4-carboxymethoxy-5-chloro-6-methylbenzaldehyde and β-alanine (Compound No. 30).

* * * * *